US011383017B1

(12) United States Patent
McCall, Jr. et al.

(10) Patent No.: US 11,383,017 B1
(45) Date of Patent: Jul. 12, 2022

(54) BONE DUST COLLECTION CAP AND PLUNGER ASSEMBLY

(71) Applicant: Tobra Medical, Inc., Wake Forest, NC (US)

(72) Inventors: Charles Edward McCall, Jr., Fuquay Varina, NC (US); Andrew John Corson, Apex, NC (US); Jay Colton Zignego, Bahama, NC (US); Theodore Jay Mosler, Raleigh, NC (US)

(73) Assignee: Tobra Medical, Inc., Wake Forest, NC (US)

( * ) Notice: Subject to any disclaimer, the term of this patent is extended or adjusted under 35 U.S.C. 154(b) by 0 days.

(21) Appl. No.: 17/489,660

(22) Filed: Sep. 29, 2021

(51) Int. Cl.
*A61M 1/00* (2006.01)
*A61B 50/36* (2016.01)
(Continued)

(52) U.S. Cl.
CPC .............. *A61M 1/67* (2021.05); *A61M 1/79* (2021.05); *A61M 1/815* (2021.05); *A61M 1/84* (2021.05); *A61M 1/88* (2021.05); *A61B 10/02* (2013.01); *A61B 10/025* (2013.01); *A61B 10/0283* (2013.01); *A61B 17/1635* (2013.01); *A61B 17/32002* (2013.01); *A61B 50/36* (2016.02); *A61B 2010/0258* (2013.01); *A61B 2017/00969* (2013.01); *A61B 2217/005* (2013.01); *A61F 2/28* (2013.01); *A61F 2/4601* (2013.01); *A61F 2/4644* (2013.01); *A61F 13/00068* (2013.01); *A61F 2002/2835* (2013.01); *A61F 2002/4649* (2013.01); *A61F 2002/4685* (2013.01); *A61M 1/60* (2021.05); *A61M 1/78* (2021.05); *A61M 1/784* (2021.05); *A61M 2202/0014* (2013.01);
(Continued)

(58) Field of Classification Search
CPC .... A61M 1/79; A61M 1/0001; A61M 1/0023; A61M 1/0058; A61M 2205/7545; A61M 2210/02; A61M 1/60; A61M 1/784; A61M 2202/0014; A61M 1/78; A61B 10/025; A61B 10/0283; A61B 2017/00969; A61B 17/1635; A61B 2217/005; A61B 17/32002; A61B 2010/0258; A61B 50/36; A61B 10/02; A61F 2/4644; A61F 2002/4649; A61F 2002/2835; A61F 2002/4685; A61F 2/4601; A61F 13/00068; A61F 2/28; C12N 5/0653
See application file for complete search history.

(56) References Cited

U.S. PATENT DOCUMENTS

| 5,478,586 A * | 12/1995 | Connor ................... A47J 31/20 426/433 |
| 2006/0052760 A1 * | 3/2006 | Batzdorf ................. A61M 1/79 604/319 |

(Continued)

*Primary Examiner* — Kai H Weng
(74) *Attorney, Agent, or Firm* — Kevin E Flynn; Flynn IP Law

(57) ABSTRACT

A surgical collection assembly for filtering material from liquid obtained during surgery has a distal plunger plate that is used to compress collected material that is filtered from liquid and entrained materials gathered during surgery. The distal plunger plate needs to be maintained above the collection jar inlet during collection of the liquid and entrained material. This disclosure teaches several ways to reversibly retain the distal plunger plate above the collection jar inlet. Also taught is a drape clamp that can affix the assembly and related tubing to a drape.

11 Claims, 26 Drawing Sheets

(51) Int. Cl.
  *A61B 10/02* (2006.01)
  *A61B 17/00* (2006.01)
  *A61B 17/16* (2006.01)
  *A61B 17/32* (2006.01)
  *A61F 2/46* (2006.01)
  *A61F 13/00* (2006.01)
  *A61F 2/28* (2006.01)
  *C12N 5/077* (2010.01)

(52) U.S. Cl.
  CPC . *A61M 2205/7545* (2013.01); *A61M 2210/02* (2013.01); *C12N 5/0653* (2013.01)

(56) References Cited

U.S. PATENT DOCUMENTS

2007/0225665 A1* 9/2007 Perez-Cruet ............ A61M 1/79
  604/317
2017/0056032 A1* 3/2017 Look ................. A61M 1/732
2018/0280623 A1* 10/2018 Pilkington ........ A61M 5/31515

* cited by examiner

FIG. 1 Prior Art
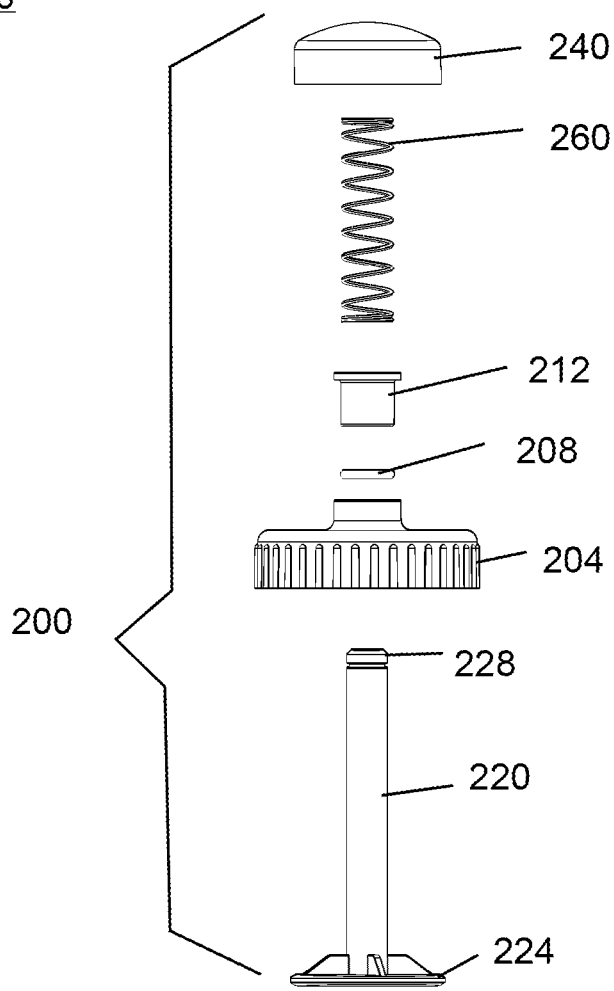
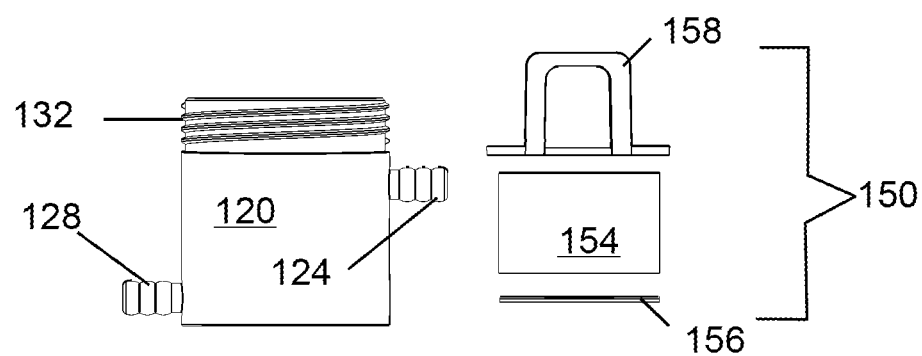

100

<u>480</u>

480

<u>480</u>

480

480

480

480

480

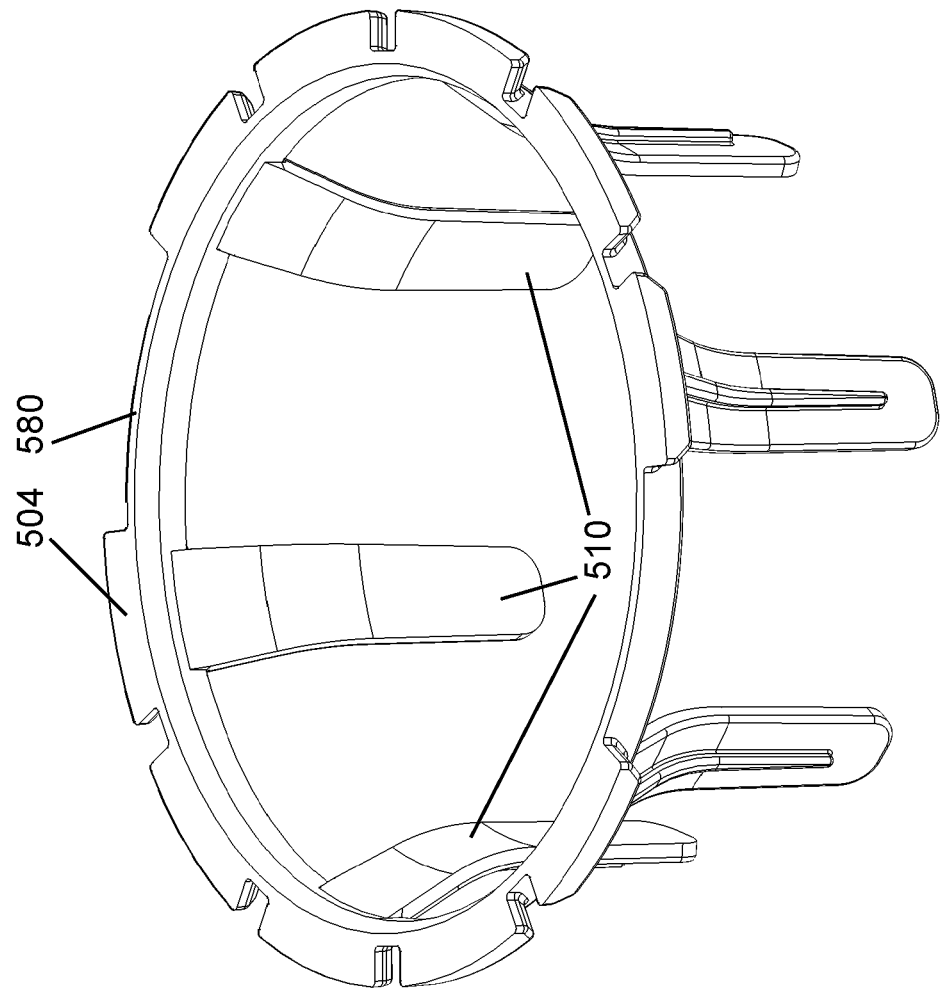

600

600

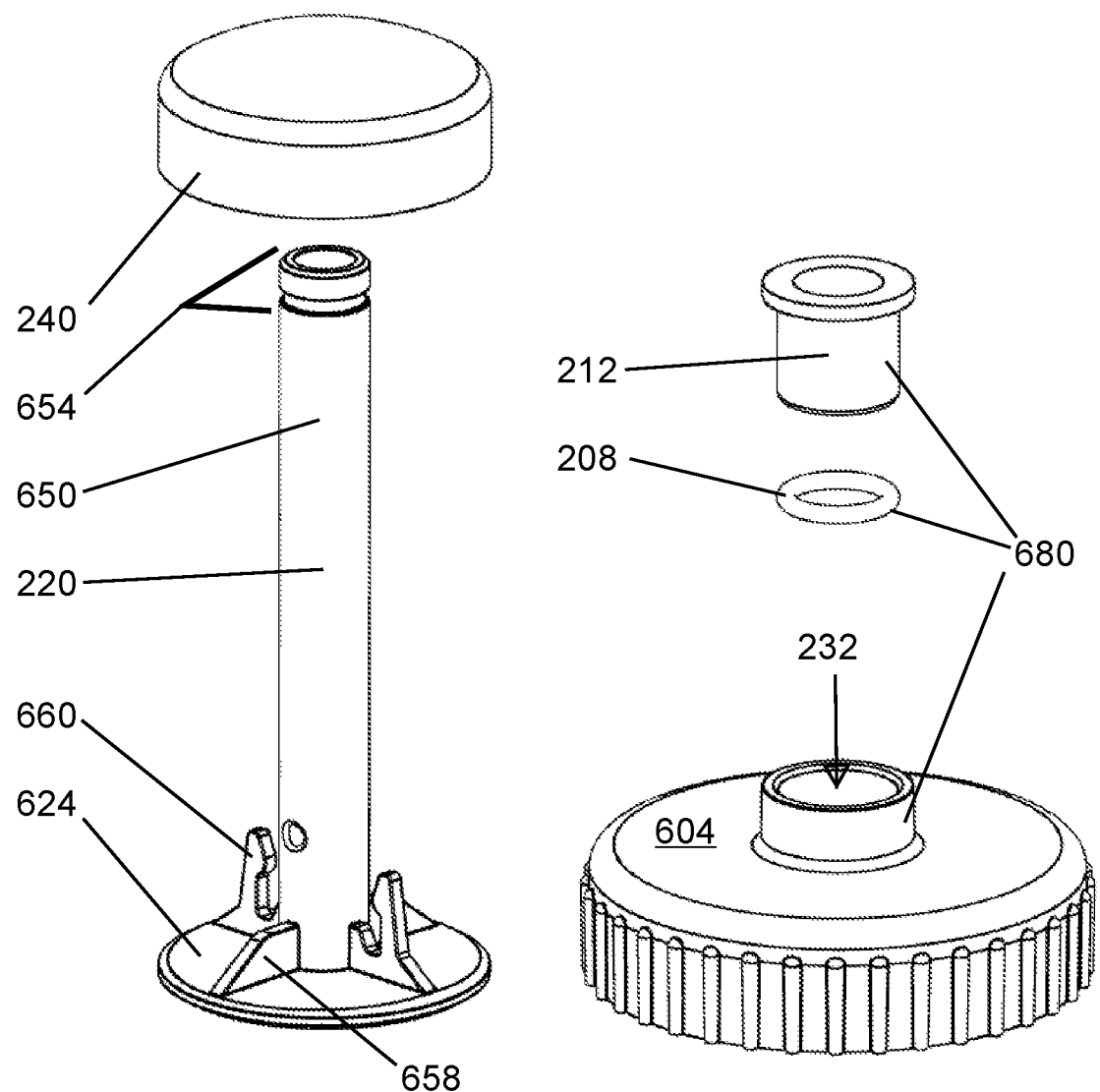

| 2004 | Connect a drape clamp to the combination of the surgical collection assembly and associated tubing. |

| 2008 | Hyper-cross the legs of the drape clamp. |

| 2012 | Insert a portion of drape material in a gap between fingers of the drape clamp while the drape clamp legs are hyper-crossed. |

| 2016 | Release the drape clamp so that the fingers on each crossed leg move toward the other leg to form a serpentine path for the captured drape material to form a reversible engagement between the surgical collection assembly and the drape. |

180

BONE DUST COLLECTION CAP AND PLUNGER ASSEMBLY

This application builds upon a series of applications filed on behalf of assignee. In particular this application extends the innovative work in the area of collection systems for use during surgery described in commonly assigned U.S. Pat. No. 9,872,944 for Collection System for Surgical Use and U.S. Pat. No. 10,940,247 for Collection Jar and Collection Basket for Surgical Use. This application claims priority and claims the benefit of co-pending and commonly assigned U.S. Provisional Patent Application No. 63/113,561 for Bone Dust Collection System. This application incorporates by reference herein the contents of the '944 patent, the '247 patent, and the '561 application, with the provision that any discrepancies between the teachings of the incorporated documents and the present disclosure are to be resolved in favor of the present disclosure.

BACKGROUND

Field of the Disclosure

This disclosure relates generally to systems that collect surgical samples via suction and filtration. More particularly to systems that are adapted to collect bone material that will be used in a surgical procedure.

Related Art

As this application extends the innovative work in the area of collection systems for use during surgery described in U.S. Pat. No. 9,872,944 for Collection System for Surgical Use, it is efficient and helpful to the Examiner to review what was taught in the '944 application.

FIG. 1 shows an exploded front view of a surgical collection assembly 100. Visible in FIG. 1 are jar 120 with inlet 124 and outlet 128. The inlet 124 and outlet 128 may have a shape designed to retain tubing such as a barbed profile. Jar 120 has a set of male threads 132 for engaging a corresponding set of female threads 216 (not shown here) within cap 204.

A basket ring 158 is used to position a basket 150 within the jar 120 to allow the basket to collect material filtered from a flow of suctioned material taken from the surgical site. The basket 150 may be constructed so that a basket sidewall 154 is connected to a basket bottom 156.

Suction applied to the outlet 128 of the jar 120 through suction side tubing (not shown) pulls liquid and entrained material from the surgical site into surgical side tubing (not shown) into the inlet 124 of jar 120 and into the basket 150. Suction pressure removes much of the liquid content of the liquid and entrained material provided to the basket 150 as the basket 150 serves as a filter to separate non-liquids from the liquid removed from the surgical site.

A plunger assembly 200 has plunger rod 220 with a distal plunger plate 224 that may be moved to compress the contents of the basket 150 to remove additional fluids from the collected material. The plunger rod 220 has a proximal end 228 that fits through a bore 232 (not visible here). The bushing 212 and O-ring 208 help maintain a vacuum seal around the plunger rod 220. The bushing 212 is press fit into the bore 232 to capture the O-ring 208 to tightly fit around plunger rod 220 and inside the bore to provide an adequate vacuum seal. The vacuum seal does not need to be perfect, but should be sufficient so that suction applied to the outlet 128 to provide suction to the inlet 124 is sufficient for use in pulling material from the surgical site. If the opening at the surgical site is covered by something that cannot be pulled into the opening, then the suction may pull some air through the seal around the plunger rod 220 but small quantities of in-leakage are not a problem.

The proximal end 228 of plunger rod 220 fits through the interior of spring 260 and into a bore in plunger rod handle 240. The connection between the proximal end 228 of the plunger rod 220 and the bore in the plunger rod handle 240 may be made in a number of ways. The connection may be a threaded connection and thus reversible. The connection may be a non-reversible connection made via any of a number of techniques known to those of skill in the art including a snap fit. Gluing may be used instead of a snap fit if there is a desire for a secure connection.

The spring 260 holds the plunger rod 220 in an elevated position with the distal plunger plate 224 of the plunger rod 220 above the flow of material entering the jar 120 through the inlet 124. The plunger rod handle 240 may be pushed down against the spring force to push the distal plunger plate 224 of the plunger rod 220 downward to compress material collected in the basket 150 to further remove fluid.

FIG. 2 provides a front view of the surgical collection assembly 100. FIG. 3 shows a cross section of the view from FIG. 2 taken through the midlines of the inlet 124 and outlet 128.

Visible in FIG. 2 and FIG. 3 are previously referenced elements: plunger rod handle 240, plunger rod 220, spring 260, bushing 212, cap 204, inlet 124, jar 120, and outlet 128.

Additional elements visible in FIG. 3 that are not visible in FIG. 2 include: O-ring 208 resting on ledge 236 in bore 232, proximal end 228 of plunger rod 220, distal plunger plate 224 of plunger rod 220, basket ring 158, basket 150, female threads 216 on cap 204, and male threads 132 on jar 120.

Note that FIG. 3 provides a view of the seal around the plunger rod 220 as the bushing 212 encloses the O-ring 208 between the bushing 212 and the ledge 236 within the bore 232 of the cap 204.

A careful observer will note that the model shows the O-ring 208 in the shape it assumes before engagement with the uncapped plunger rod 220. The O-ring is compressed between the plunger rod 220 and the cap 204. However, the bushing 212 is not designed to compress the O-ring 208.

FIG. 4 shows the plunger rod 220 moved downward so that the distal plunger plate 224 of the plunger rod 220 is just above the basket bottom 156. Force applied to the plunger rod handle 240 has compressed the spring 260. Also visible in this view is cap 204 and basket ring 158. In order to show the relationship between the distal plunger plate 224 of the plunger rod 220 and the basket bottom 156, the jar 120 and sidewalls of the basket 150 have been made invisible.

After releasing the plunger rod handle 240, the distal plunger plate 224 of the plunger rod 220 will move upward relative to the basket 150 as the spring force is sufficient to return the plunger rod handle 240 to the upper position. It is possible that during the compression of collected material that some collected material may fill any void between the outer perimeter of the distal plunger plate 224 of the plunger rod 220 in the inner perimeter of the basket 150. To minimize any tendency to lift the basket 150 out of position, the basket ring 158 has a pair of handles 162 (one handle visible in FIG. 3). The top edge 160 of the handle 162 is positioned very close to the inside face 206 of the cap 204 so that the distal plunger plate 224 of the plunger rod 220 continues to move upward after the top edge 160 of the handle 162 strikes the inside face 206 of the cap 204 so that the basket 150 becomes dislodged from the distal plunger plate 224 of the plunger rod 220.

Placement of Inlet and Outlet on Jar.

Note that by having both the inlet 124 and the outlet 128 located on the jar 120 and not split between the jar 120 and the cap 204, rotating the plunger & cap assembly 200 to remove the plunger & cap assembly 200 to expose the interior of the jar 120 may be done without disconnecting the vacuum side tubing connecting the outlet 128 to the vacuum source and without disconnecting the surgical side tubing connected to the inlet 124. Thus neither the connection of tubing to the inlet 124 or to the outlet 128 needs to be a more expensive quick disconnect connection such as a bayonet connection.

Allowing quick removal of the plunger & cap assembly 200 from the surgical collection assembly 100 to expose the basket 150 allows collected material to be removed and a new basket 150 to be inserted. As the connections to the inlet 124 and outlet 128 are in place, the process of collecting can resume quickly after the plunger & cap assembly 200 is re-engaged with the jar 120.

A second advantage of having the inlet 124 on the jar 120 rather than on the cap 204 is that this placement helps keep material coming in through the inlet from getting up on the top side of the distal plunger plate 224 of the plunger rod 220. This avoids wasting material that could have been collected in the basket 150 and reduces the opportunity for material to interfere with the operation of the plunger rod 220.

When using the plunger rod 220 to press the collected material, an operator may wish to lift the surgical end of the surgical side tubing out of the surgical site so that only air is entering the inlet 124. The suction source may be left on during this process to help remove fluids that are pressed out of the collected material.

As the plunger assembly is of focus in the present application, a set of additional views of the plunger assembly from the '944 patent is provided.

FIG. 5 is a top perspective view of plunger & cap assembly 480.

FIG. 6 is a bottom perspective view of plunger & cap assembly 480.

FIG. 7 is a side view of plunger & cap assembly 480.

FIG. 8 is a top plan view of plunger & cap assembly 480.

FIG. 9 is a bottom plan view of plunger & cap assembly 480.

FIG. 10 is a side view of a cross section of FIG. 9.

FIG. 11 is a top, side perspective view of a cross section of FIG. 9.

FIG. 12 is a top, side perspective view of a cross section of FIG. 9.

United States Provisional Patent Application No. 63/113,561.

The application builds upon the teachings found in U.S. Provisional Patent Application No. 63/113,561 for Bone Dust Collection System. This application teaches the use of a finger ring. While this application is not prior art to the present application, to help with the focus on what is new in this application, the teachings from the '561 application are discussed here.

FIG. 13 shows a basket 454 that has basket sidewalls 154 pressed inwardly by a set of finger springs 510 extending from an upper portion 504 of finger ring 500 towards the basket bottom 156. Thus, movement of the distal plunger plate 224 will make contact with the inwardly pressed basket sidewalls 154 which will dislodge bone material and other items that are on the basket sidewalls 154. Removing material from the basket sidewalls 154 will tend to increase the ability of fluid to flow out of the basket while in use and subject to vacuum pressure applied to the jar outlet.

FIG. 14 shows finger ring 500 in isolation. Finger ring 500 has an upper portion 504 that fits just under basket ring 358 (FIG. 13). The finger ring 500 has a number of finger springs 510 that push the basket sidewalls 154 inward so that movement of the distal plunger plate 224 of plunger rod 220 is resisted by the finger springs 510 that are covered by portions of the basket sidewalls 154. While resistance is not sufficient to preclude easy movement of the plunger rod 220, the movement of the distal plunger plate 224 of plunger rod 220 now scrapes bone dust material from portions of the basket sidewalls 154 to enhance the removal of fluid through the basket sidewalls 154 under the influence of suction applied to the surgical collection assembly 100.

The '561 application has several embodiments and additional detail but this review is sufficient to introduce the finger ring 500 which will be visible in some figures for the present disclosure.

Vocabulary.

A, An.

In this application, and the claims that follow, the terms a, an, or the identification of a single thing should be read as at least one unless such an interpretation is impossible within the context of the entirety of the specification. For example, the use of the terms sole, only, or the phrase not more than one would indicate that a single item is intended.

Gne and Gnes.

To avoid the awkward he/she and his/her or the potentially confusing singular use of they and their, this application uses the gender-neutral pronoun gne and the possessive gnes.

Or.

Unless explicit to the contrary, the word "or" should be interpreted as an inclusive or rather than an exclusive or. Thus, the default meaning of or should be the same as the more awkward and/or.

Proximal and Distal.

Proximal and distal should be considered relative to the user. Thus the proximal end of the component is the portion of the component that is closest to the user when using the device. In this instance, a user compressing collected material would be handling plunger rod handle 240 which would thus be proximal to gner and the bottom of the jar 120 would be distal to gner.

Set.

Unless explicit to the contrary, the word "set" should be interpreted as a group of one or more items.

Step.

The term step may be used in descriptions within this disclosure. For purposes of clarity, one distinct act or step may be discussed before beginning the discussion of another distinct act or step. The term step should not be interpreted as implying any particular order among or between various steps disclosed unless the specific order of individual steps is expressly indicated.

Substantially.

Frequently, when describing an industrial process it is useful to note that a given parameter is substantially met. Examples may be substantially parallel, substantially perpendicular, substantially uniform, and substantially flat. In this context, substantially X means that for purposes of this industrial process it is X. So something that may not be absolutely parallel but is for all practical purposes parallel, is substantially parallel. Likewise, mixed air that has substantially uniform temperature would have temperature deviations that were inconsequential for that industrial process.

As recognized in C. E. Equipment Co. v. United States, 13 U.S.P.Q.2d 1363, 1368 (Cl. Ct. 1989), the word "substantially" in patent claims gives rise to some definitional leeway—thus the word "substantially" may prevent avoidance of infringement by minor changes that do not affect the results sought to be accomplished.

SUMMARY OF THE DISCLOSURE

Aspects of the teachings contained within this disclosure are addressed in the claims submitted with this application upon filing. Rather than adding redundant restatements of the contents of the claims, these claims should be considered incorporated by reference into this summary.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provided below as one of skill in the art will recognize that inventive concepts illustrated in various examples can be combined together in order to address a specific application.

Some aspects of the teachings of the present disclosure may be expressed as a surgical collection assembly for filtering material from liquid obtained during surgery; the surgical collection assembly comprising:
a collection basket,
a collection jar, and
a plunger assembly.

Within the surgical collection assembly, the plunger assembly comprising: a jar cap assembly that can be reversibly connected to an open end of the collection jar; and a plunger device that in turn includes a distal plunger plate to compress collected material that is collected in the collection basket; and a plunger rod to pass through a bore in the jar cap assembly so that a proximal end of the plunger device may be moved by a user.

The plunger device and jar cap assembly adapted for movement to reversibly engage the plunger device with the jar cap assembly to retain the distal plunger plate in a retained position so that the distal plunger plate cannot impede ingress of liquid and entrained material entering the collection jar through an inlet port. The movement to reversibly engage the plunger device with the jar cap assembly requires an elastic deformation of at least one component.

Some aspects of the teachings of the present disclosure may be expressed as a process for disengaging a plunger device from a jar cap assembly and subsequently re-engaging the plunger device with the jar cap assembly. This process involves obtaining the surgical collection assembly comprising:
a collection jar with a collection basket;
a jar cap assembly; and
the plunger device with a distal plunger plate.

The process includes inducing a temporary elastic deformation in order to disengage the plunger device from a reversible retention in a retracted position so that the distal plunger plate does not interfere with a flow path for ingress of liquid and entrained material through an inlet port to the collection jar. Then, moving the distal plunger plate away from the jar cap assembly before using the distal plunger plate to compress collected material in the collection basket. Subsequently, moving the distal plunger plate in a proximal direction which is away from the bottom of the collection basket and toward the jar cap assembly and engaging the plunger device with the jar cap assembly in the reversible retention with the distal plunger plate in the retracted position that does not interfere with a flow path for an ingress of liquid and entrained material through the inlet port to the collection jar by elastically deforming at least one component in the surgical collection assembly.

Some aspects of the teachings of the present disclosure may be expressed as a process for connecting a combination of a surgical collection assembly and associated tubing to a drape within a sterile field. This process includes engaging a drape clamp to a portion of the surgical collection assembly and hyper-crossing a pair of legs of the drape clamp so that there is elastic deformation within the drape clamp and thus a spring force to move the pair of legs back to their original position and a gap between a first set of at least one finger on a first leg within the pair of legs and second set of at least one finger on a second leg within the pair of legs. Inserting a portion of drape material in the gap between the first set of at least one finger and the second set of at least one finger while the pair of legs are hyper-crossed and releasing the drape clamp so that first set of at least one finger moves towards the second leg and the second set of at least one finger moves towards the first leg to form a serpentine path for the portion of drape material to form a reversible engagement between the surgical collection assembly and the drape.

Other systems, methods, features and advantages of the disclosed teachings will be immediately apparent or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

FIGS. 1-12 shows views of the prior art used in the background discussion.

FIGS. 13 and 14 are from a pending and commonly assigned application.

FIG. 1 shows an exploded front view of a surgical collection assembly 100.

FIG. 2 provides a front view of the surgical collection assembly 100 from FIG. 1.

FIG. 3 shows a cross section of the view from FIG. 2 taken through the midlines of the inlet 124 and outlet 128.

FIG. 4 shows the plunger rod 220 moved downward so that the distal plunger plate 224 of the plunger rod 220 is just above the basket bottom 156.

FIG. 5 is a top perspective view of plunger & cap assembly 480.

FIG. 6 is a bottom perspective view of plunger & cap assembly 480.

FIG. 7 is a side view of plunger & cap assembly 480.

FIG. 8 is a top plan view of plunger & cap assembly 480.

FIG. 9 is a bottom plan view of plunger & cap assembly 480.

FIG. 10 is a side view of a cross section of FIG. 9.

FIG. 11 is a top, side perspective view of a cross section of FIG. 9.

FIG. 12 is a top, side perspective view of a cross section of FIG. 9.

FIG. 13 shows a basket 454 that has basket sidewalls 154 pressed inwardly by a set of finger springs 510 extending from an upper portion 504 of finger ring 500 towards the basket bottom 156.

FIG. 14 shows finger ring 500 in isolation.

FIG. 17 shows an exploded view of components found in the plunger assembly 620.

FIG. 34 shows the process 2000 for connecting a surgical collection assembly and associated tubing to a drape within a sterile field.

DETAILED DESCRIPTION

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to denote different aspects of methods employed, the term should not be interpreted as implying any particular order among or between various steps herein disclosed unless and except when the order of individual steps is explicitly described.

Figure 15:
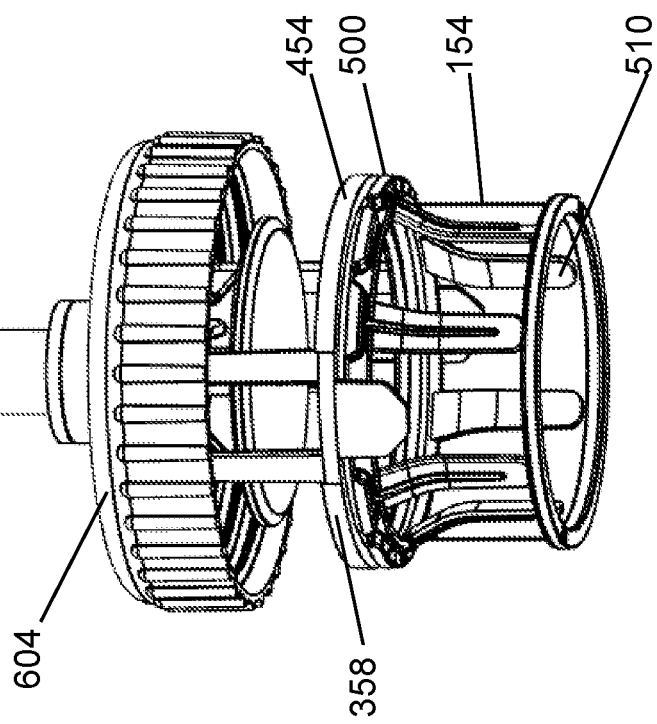
FIG. 15 has a side view of a surgical collection assembly 600 that is shown with the jar 120 hidden and the assembly rotated slightly to allow a view into the interior of the cap 604.

FIG. 15 has a side view of a surgical collection assembly 600 that is shown with the jar 120 hidden and the assembly rotated slightly to allow a view into the interior of the cap 604. Visible in this view is basket 454 with basket sidewalls 154. While the model does not accurately capture the inward movement of the basket sidewalls 154 from the pressure asserted by finger springs 510 of finger ring 500, that feature was described in detail in connection with U.S. Provisional Patent Application No. 63/113,561 for Bone Dust Collection System as discussed above.

Figure 2:
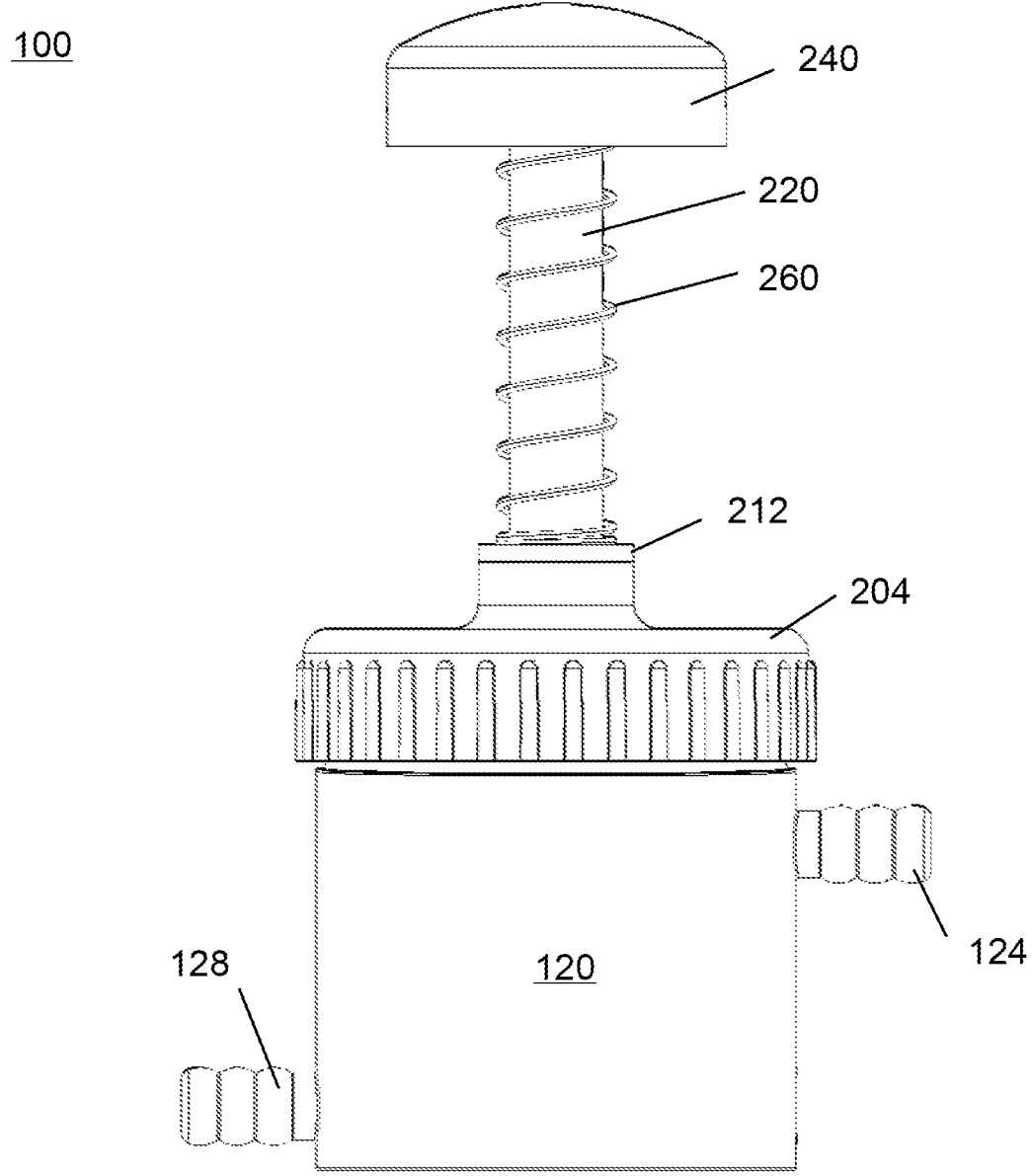
Figure 3:
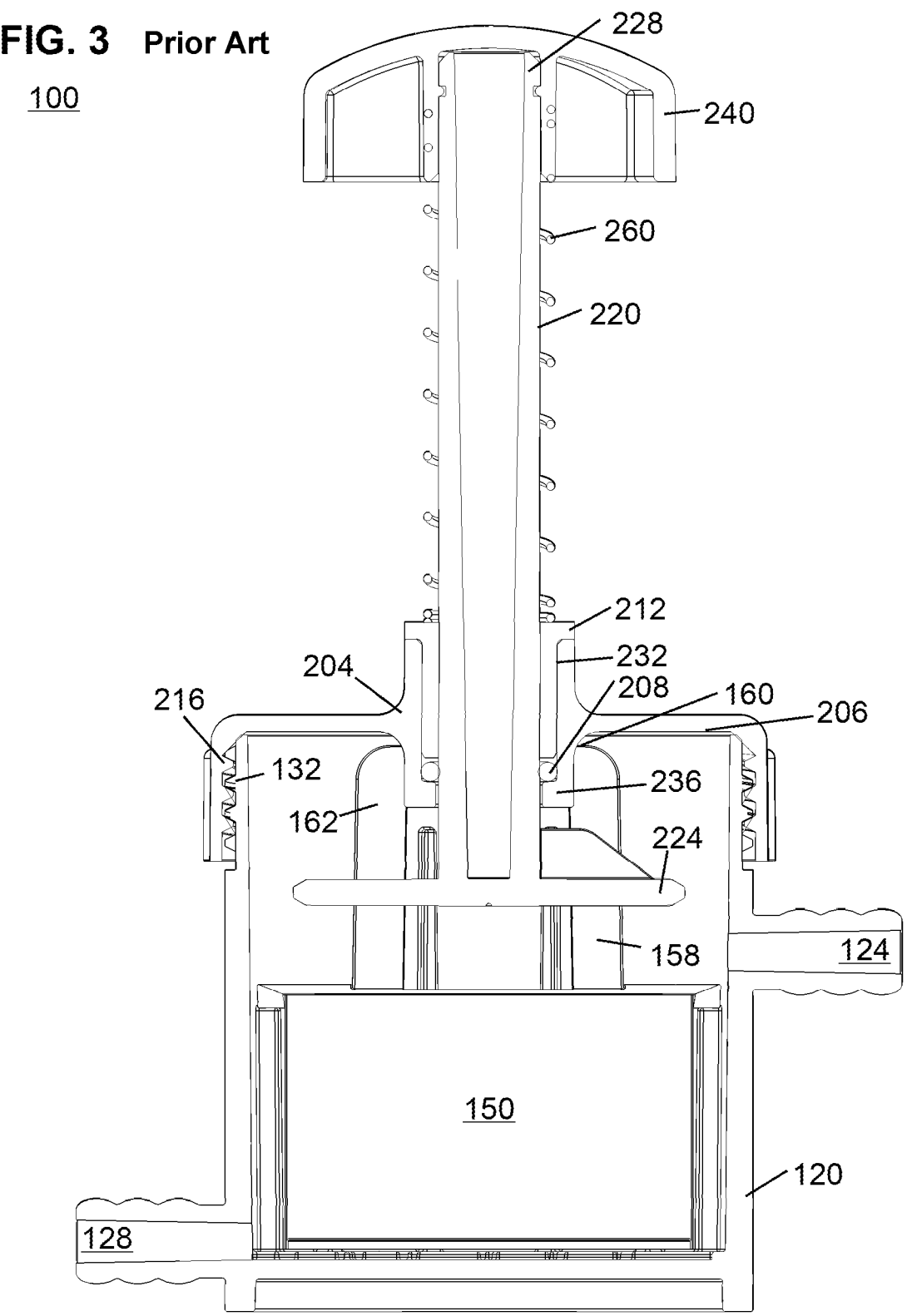
Figure 4:
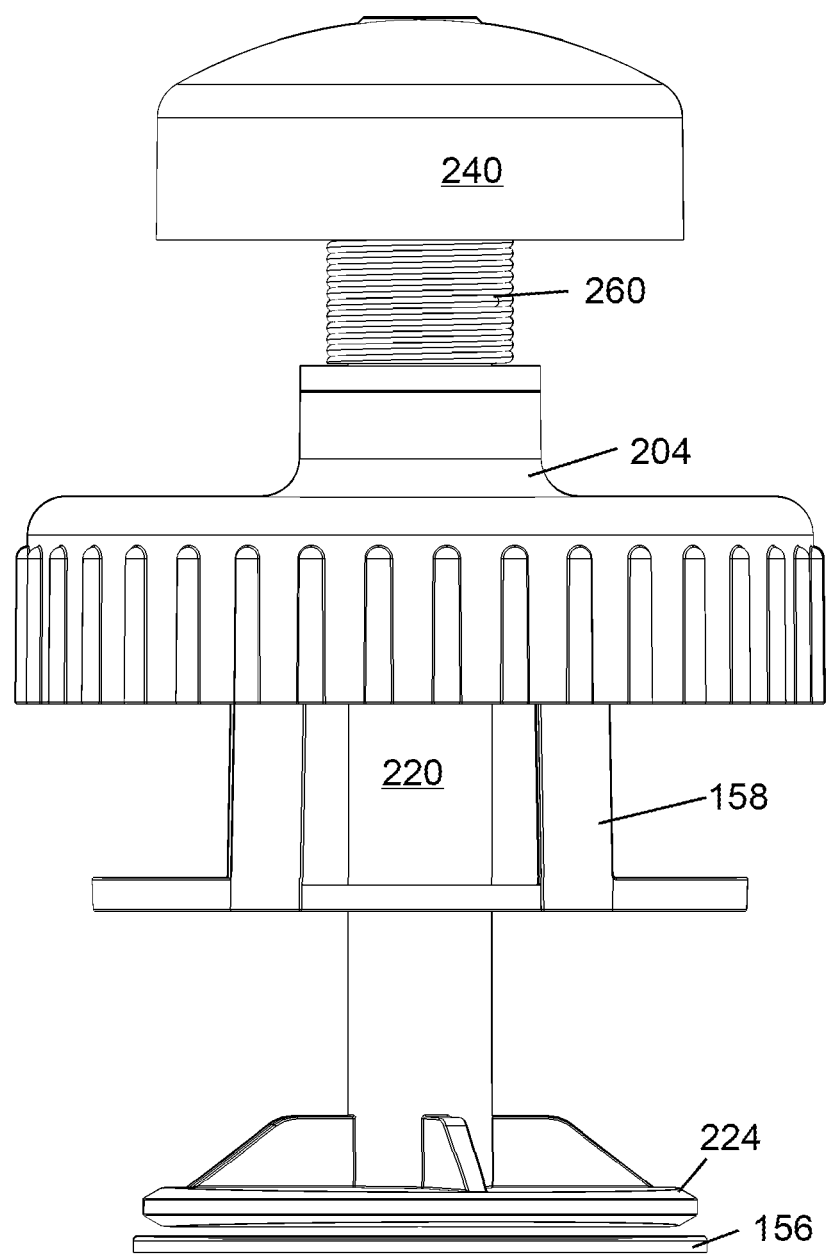
Figure 5:
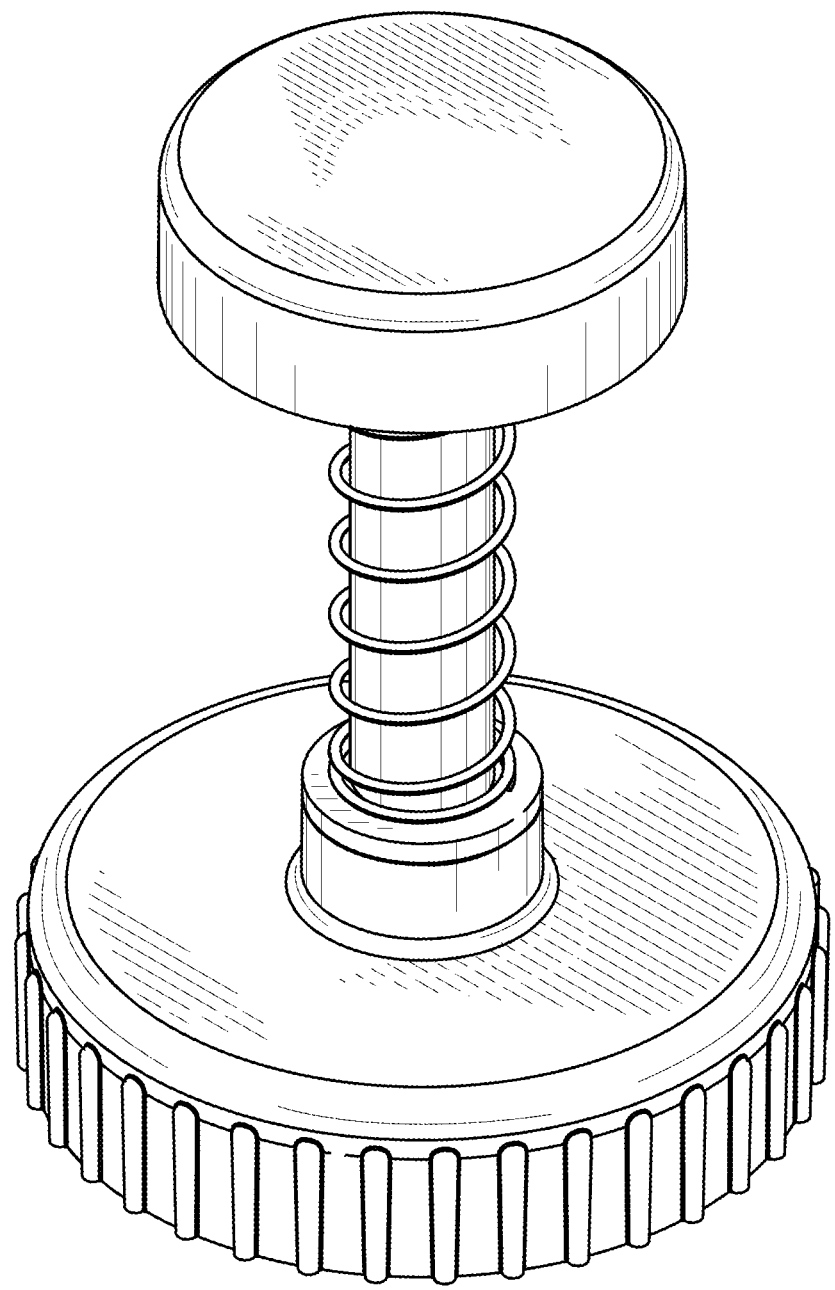
Figure 6:
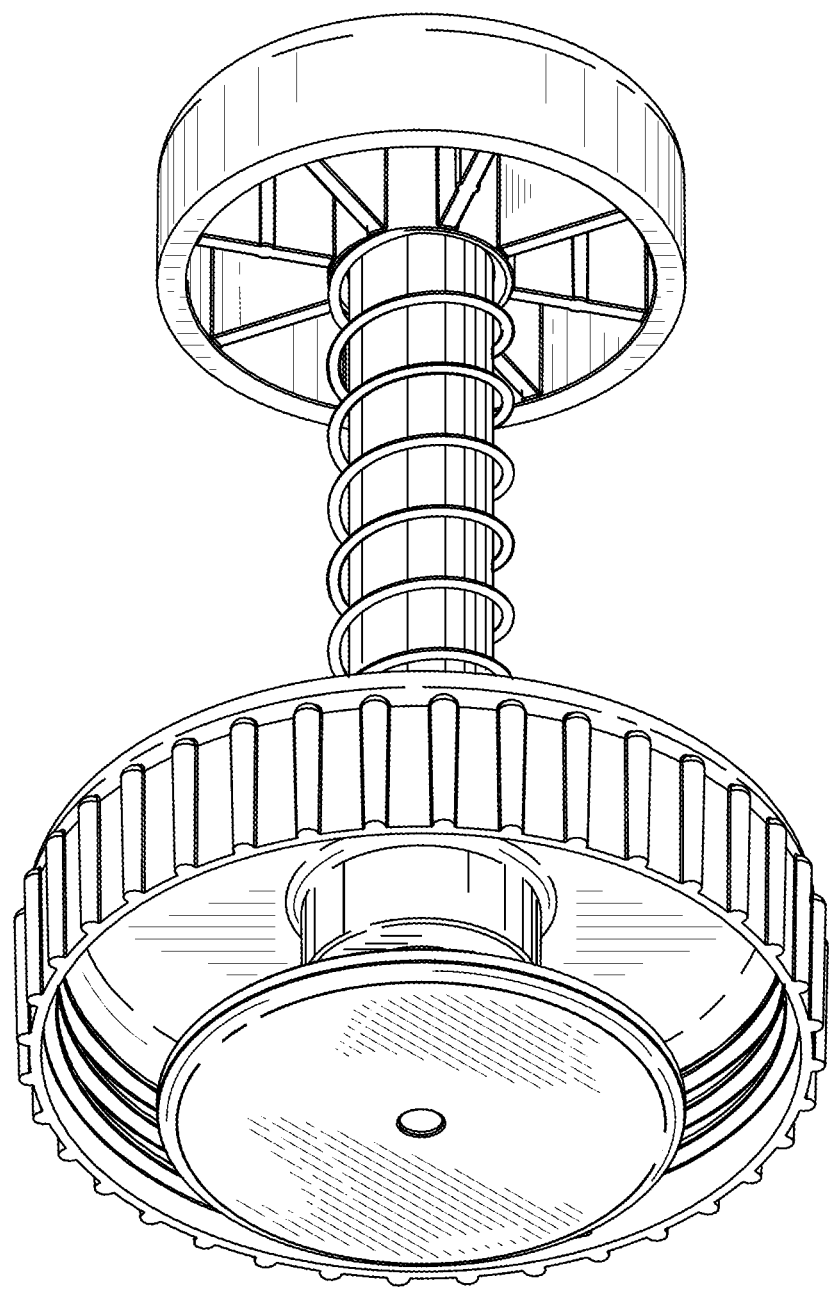
Figure 7:
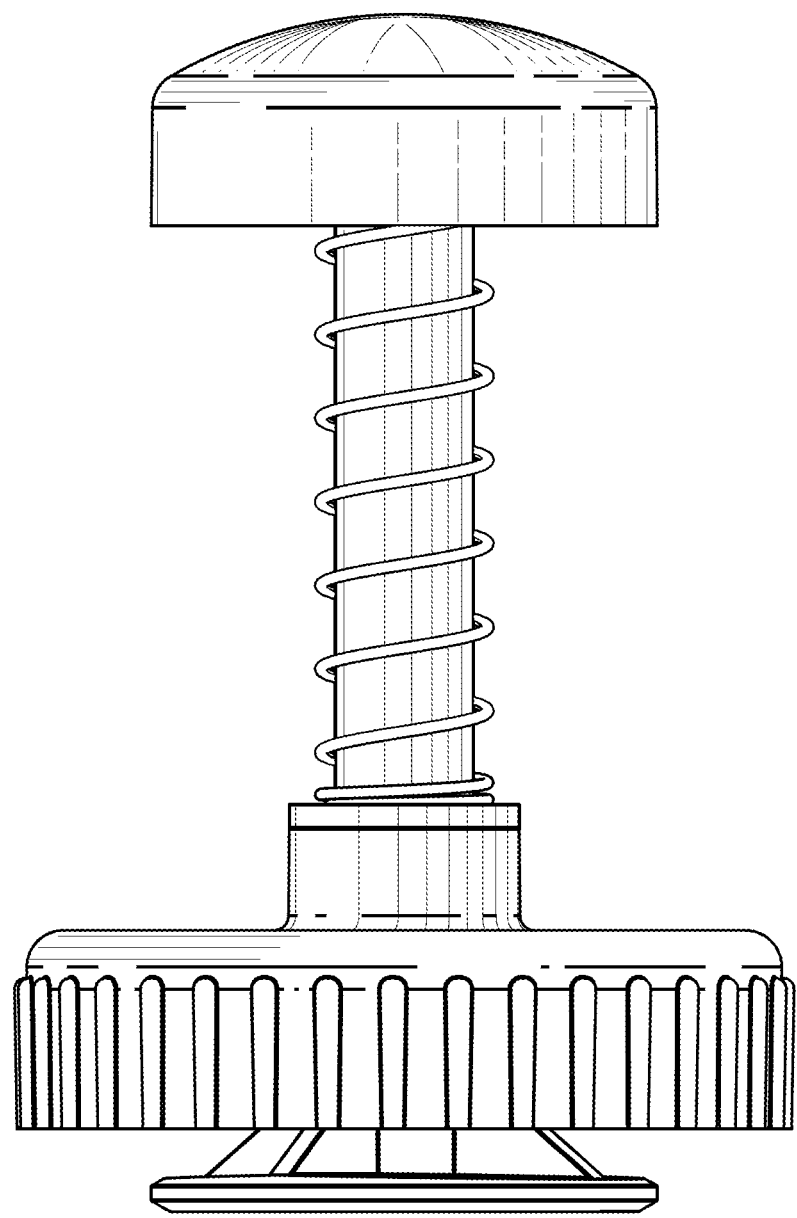
Figure 8:
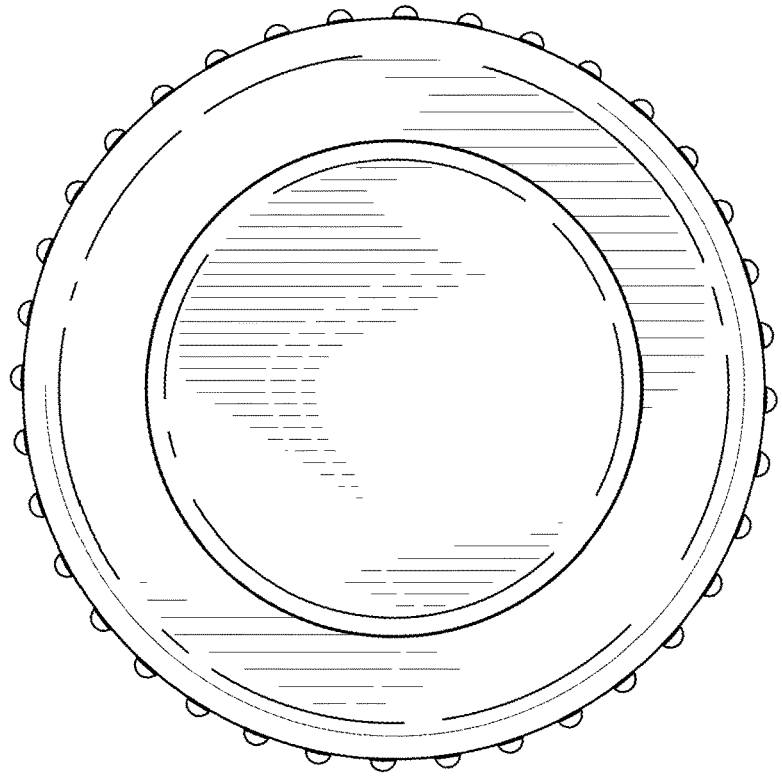
Figure 9:
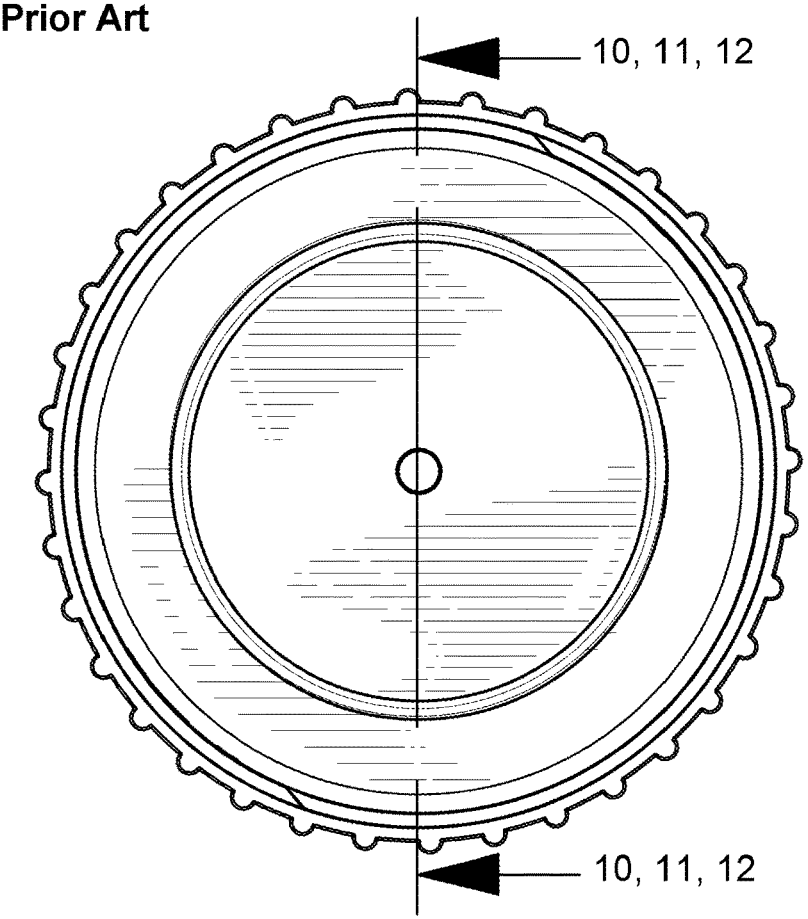
Figure 10:
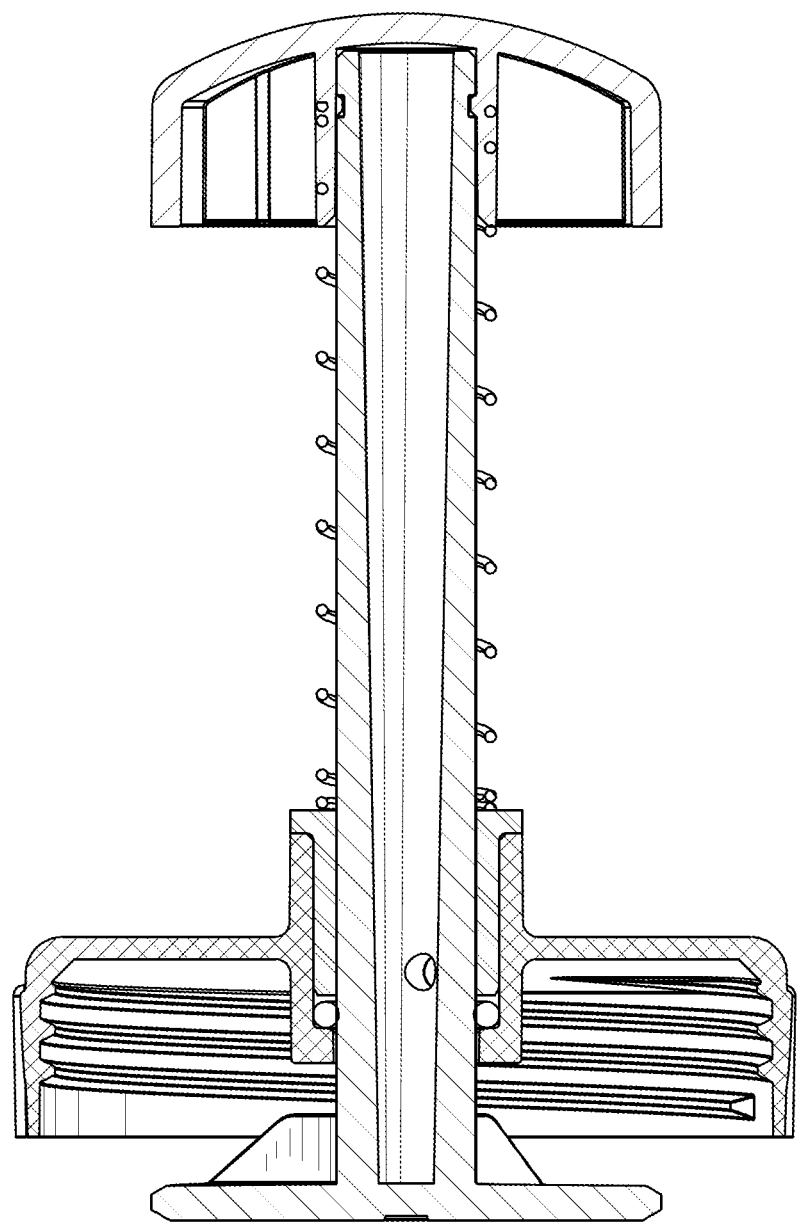
Figure 11:
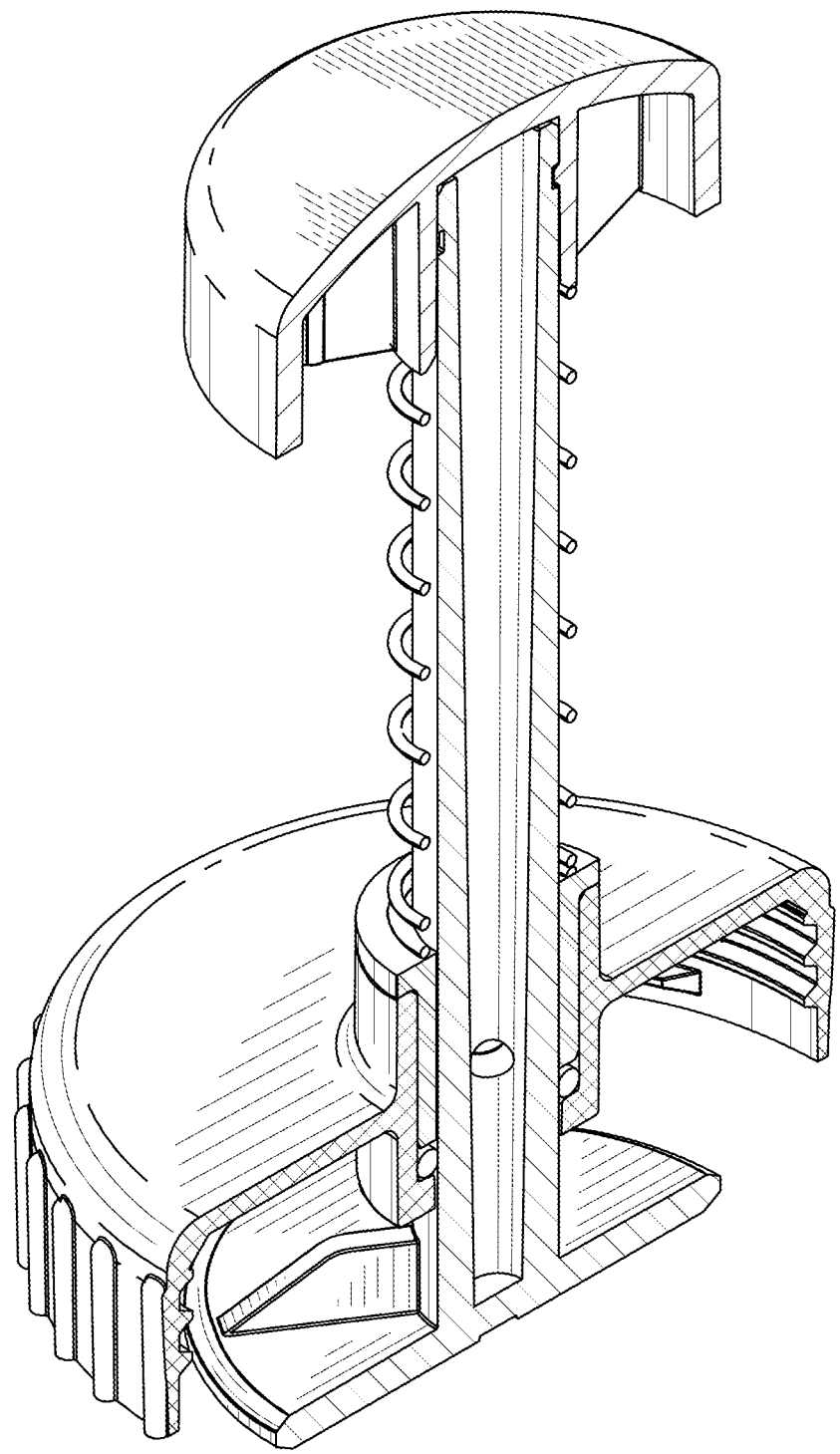
Figure 12:
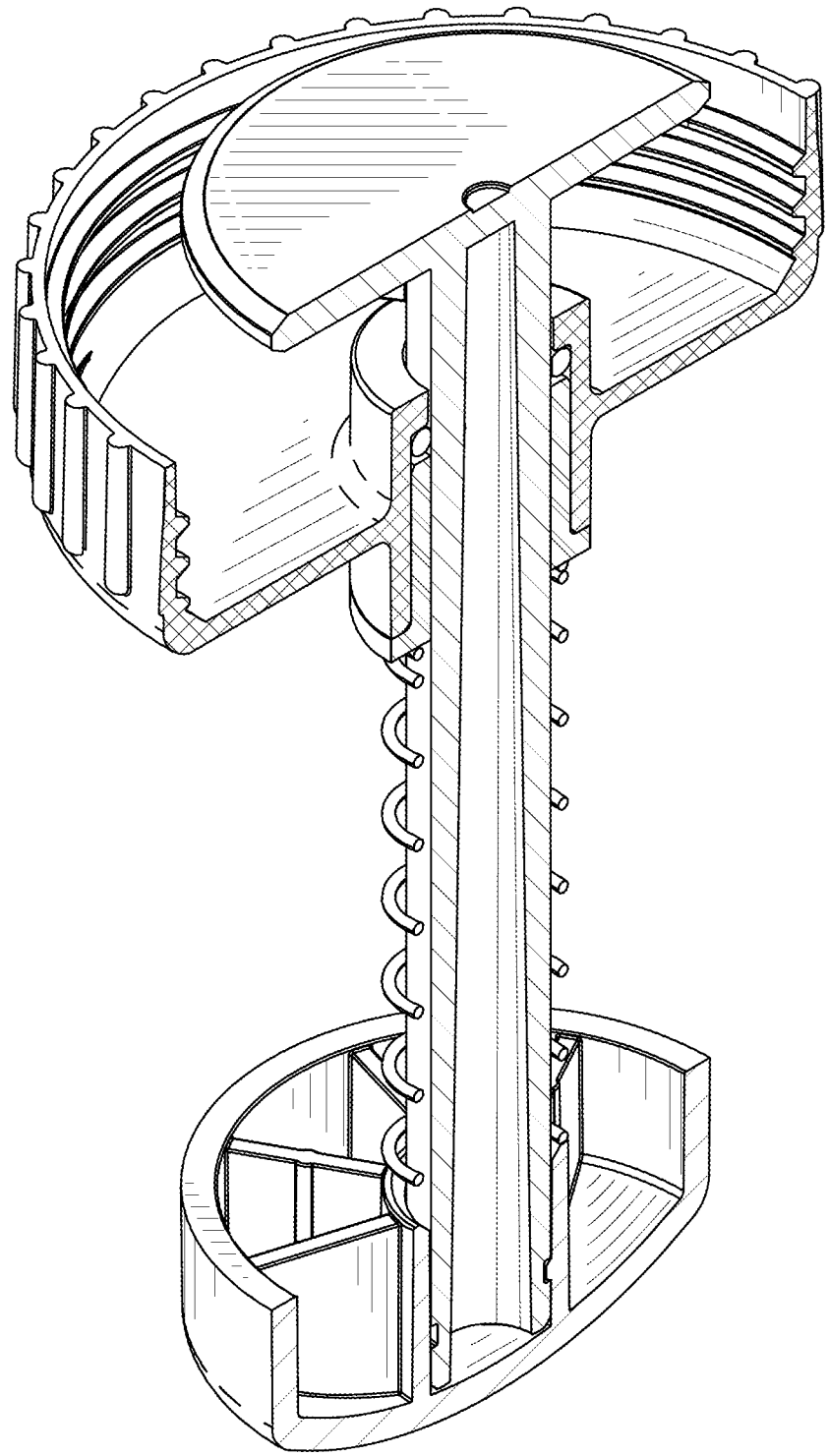
Figure 13:
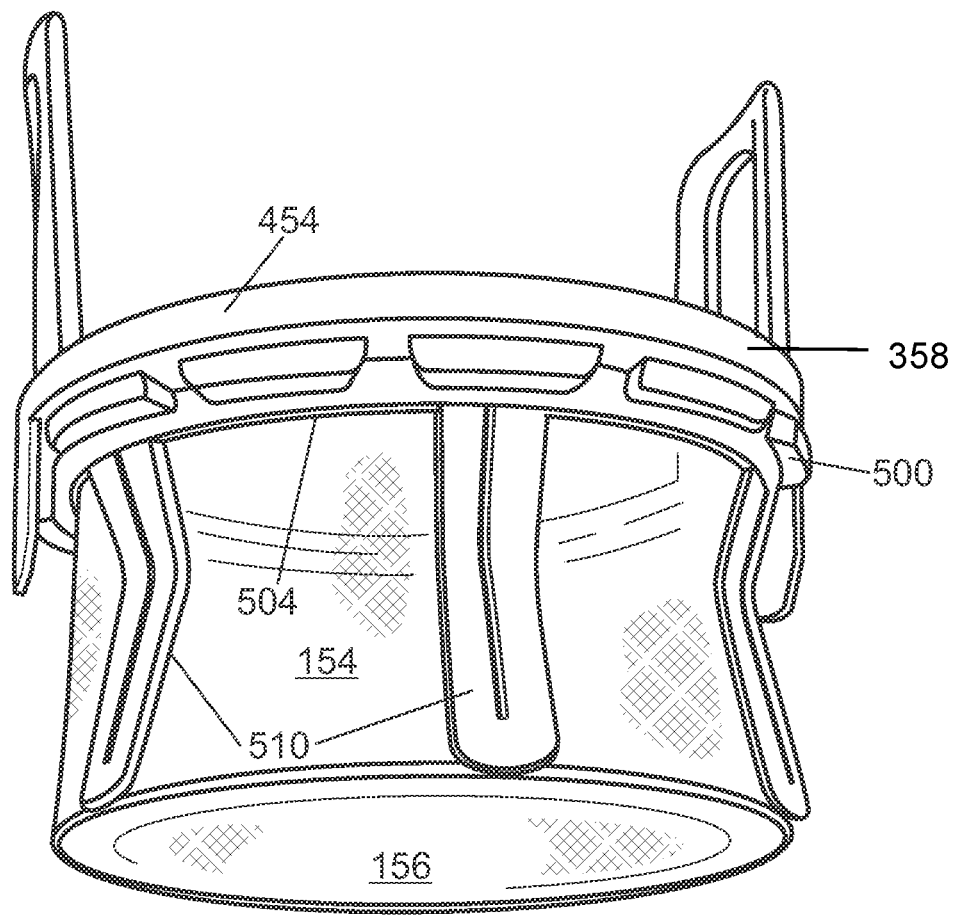
Figure 16:
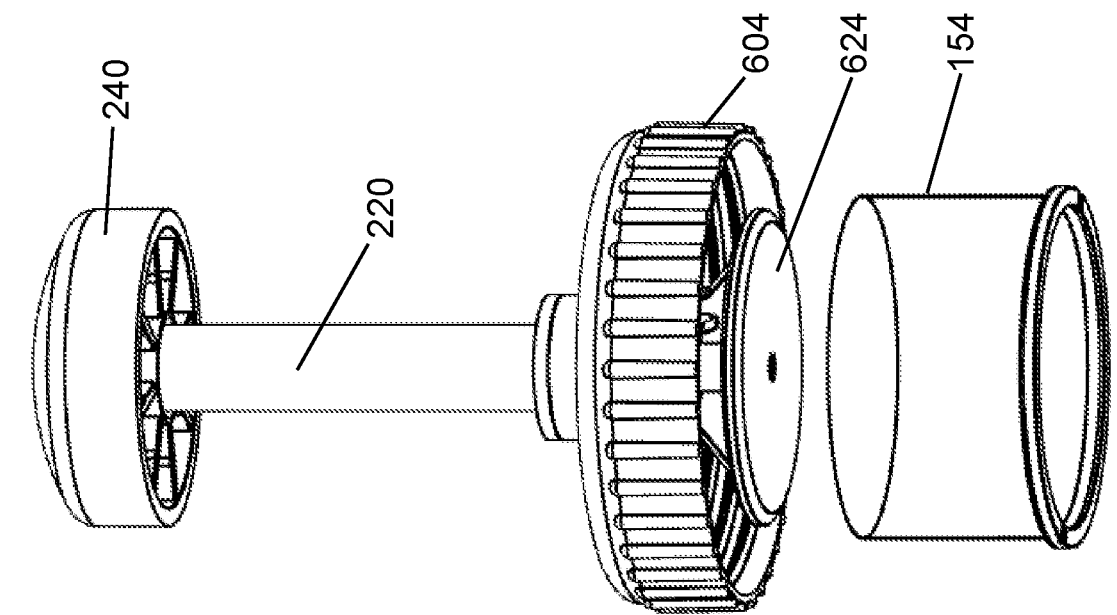
FIG. 16 has the same view of a surgical collection assembly 600 that is shown with the jar 120 hidden and the assembly rotated slightly to allow a view into the interior of the cap 604 shown in FIG. 15.

FIG. 16 has the same view of a surgical collection assembly 600 that is shown with the jar 120 hidden and the assembly rotated slightly to allow a view into the interior of the cap 604 shown in FIG. 15. The basket ring 358 has been hidden along with the finger ring 500 to allow a clean view of the basket sidewalls 154 and the distal plunger plate 624. A careful observer may note that unlike FIGS. 1-7 and 10-12 discussed above, the plunger rod 220 is not surrounded by a spring 260 to hold the distal plunger plate 624 in a raised position until the user advances the distal plunger plate 624 distally and away from the cap 604 to compress the collected material.

In contrast, for the plunger & cap assembly 200 of FIG. 1, the spring 260 holds the plunger rod 220 in an elevated position with the distal plunger plate 224 of the plunger rod 220 above the flow of material entering the jar 120 through the inlet 124. For the plunger & cap assembly 200 of FIG. 1, the plunger rod handle 240 may be pushed down against the spring force to push the distal plunger plate 224 of the plunger rod 220 downward to compress material collected in the basket 150 to further remove fluid.

The modifications of the surgical collection assembly 600 to allow for operation without spring 260 are a primary focus for this application.

FIG. 17 shows an exploded view of components found in the plunger assembly 620. A plunger assembly 620 has a plunger device 650 including optional plunger rod handle 240. The plunger assembly 620 also has a jar cap assembly 680 that includes a cap 604, bushing 212, and O-ring 208.

Plunger device 650 has a proximal end 654 for attachment to plunger rod handle 240 using any conventional attachment method. The connection may be a threaded connection and thus reversible. The connection may be a non-reversible connection made via any of number of techniques known to those of skill in the art including a snap fit. Gluing may be used instead of a snap fit if there is a desire for a secure connection.

A plunger rod 220 connects the proximal end 654 with a distal plunger plate 624 that may be moved to compress the contents of the basket 454 (FIG. 15) to remove additional fluids from the collected material. The proximal end 654 fits through a bore 232 in cap 604. The bushing 212 and O-ring 208 help maintain a vacuum seal around the plunger rod 220. The bushing 212 may be press fit into the bore 232 to capture the O-ring 208 to tightly fit around plunger rod 220 and inside the bore 232 to provide an adequate vacuum seal. The vacuum seal does not need to be perfect, but should be sufficient so that suction applied to the outlet 128 (FIG. 1) to apply suction to the inlet 124 (FIG. 1) is sufficient for use in pulling material from the surgical site into the jar 120 (FIG. 1). If the opening at the surgical site is covered by something that cannot be pulled into the opening, then the suction may pull some air through the seal around the plunger rod 220 but small quantities of in-leakage are not a problem.

Plunger device 650 includes a pair of cap hooks 660. These cap hooks 660 extend from the distal plunger plate 624 towards the proximal end 654 of the plunger device 650. As will be described in more detail below, the pair of cap hooks 660 engage with a feature on the cap 604 so that when the user moves the plunger rod handle 240 away from the cap 604, the cap hooks 660 reversibly engage with the cap 604 to hold the distal plunger plate 624 in an elevated position that does not interfere with the loading of the jar 120 (FIG. 1) with the liquid and entrained material obtained during surgery. When a user moves the plunger rod handle 240 toward the cap 604, the cap hooks 660 reversibly disengage with the cap 604 so as to no longer hold the distal plunger plate 624 in an elevated position that does not interfere with the loading of the jar 120 (FIG. 1) with the liquid and entrained material obtained during surgery. The distal plunger plate 624 may be used by the user to compress collected material within the collection basket 150 (FIG. 1) to help remove fluid from the collected material.

A secondary benefit of the pair of cap hooks 660 is to add additional structural support via connections between the distal plunger plate 624 and the plunger rod 220. This can be further augmented through the use of one or more plate braces 658 which add additional connections between the distal plunger plate 624 and the plunger rod 220 but do not engage with the cap 604.

One of skill in the art will appreciate that the teachings of the present disclosure are not limited to having exactly two cap hooks 660 or having exactly two plate braces 658. One could choose to have no plate braces 658 and perhaps additional cap hooks 660. The spacing of cap hooks 660 and plate braces 658 do not need to be on 90-degree intervals. For example, the cap hooks 660 could be on 120-degree intervals. The angular spacing does not need to be uniform although many designers will prefer a uniform spacing between cap hooks 660.

Figure 19:
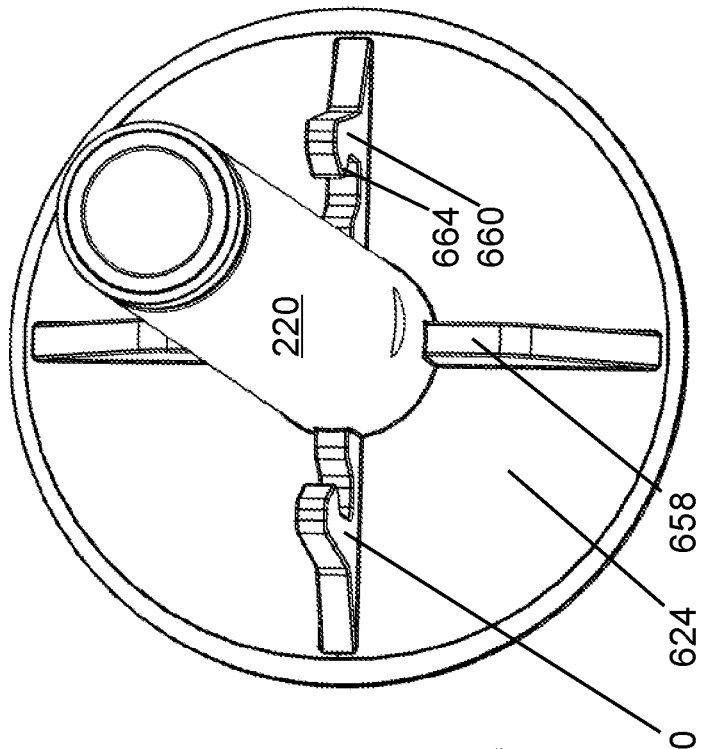
FIG. 19 is top perspective view of the plunger device 650 that has been tilted to show details of the cap hooks 660 and plate braces 658.
Figure 18:
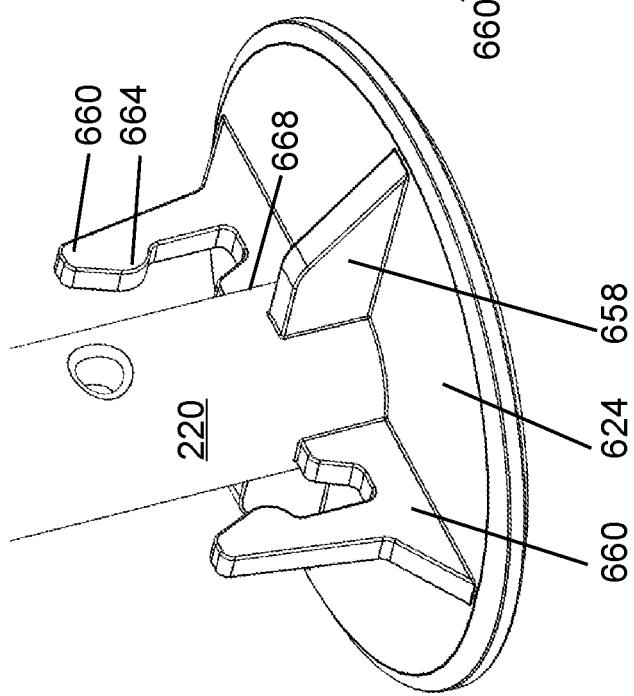
FIG. 18 is an enlarged partial view of the distal end of plunger device 650 that has been tilted to show details of the cap hooks 660 and plate braces 658.

FIG. 18 is an enlarged partial view of the distal end of plunger device 650 that has been tilted to show details of the cap hooks 660 and plate braces 658. Likewise, FIG. 19 is a top perspective view of the plunger device 650 that has been tilted to show details of the cap hooks 660 and plate braces 658. Cap hooks 660 shown here have protrusion 664 that engages with a portion of the cap 604. Note that while the protrusion 664 extends radially inward towards a longitudinal centerline of the plunger rod 220, those of skill in the art will appreciate that the protrusion could have extended radially outward away from the longitudinal centerline of the plunger rod 220 or in any other direction as long as the cap 604 has a corresponding engagement feature to allow the protrusion 664 to reversibly engage with the engagement feature of the cap 604.

Thus, some embodiments may not require a specific angular relationship between the plunger assembly and the jar cap. Other embodiments may require a specific angular relationship between the plunger assembly and the jar cap. Those of skill in the art will appreciate that markings on the plunger assembly and jar cap may expedite a process that require a specific angular relationship between the plunger assembly and the jar cap but such markings are not strictly required.

Those of skill in the art will appreciate that there can be advantages to having the protrusion 664 point radially inward or radially outward to engage a circular engagement feature so that there is not a need for alignment markers.

Figure 20:
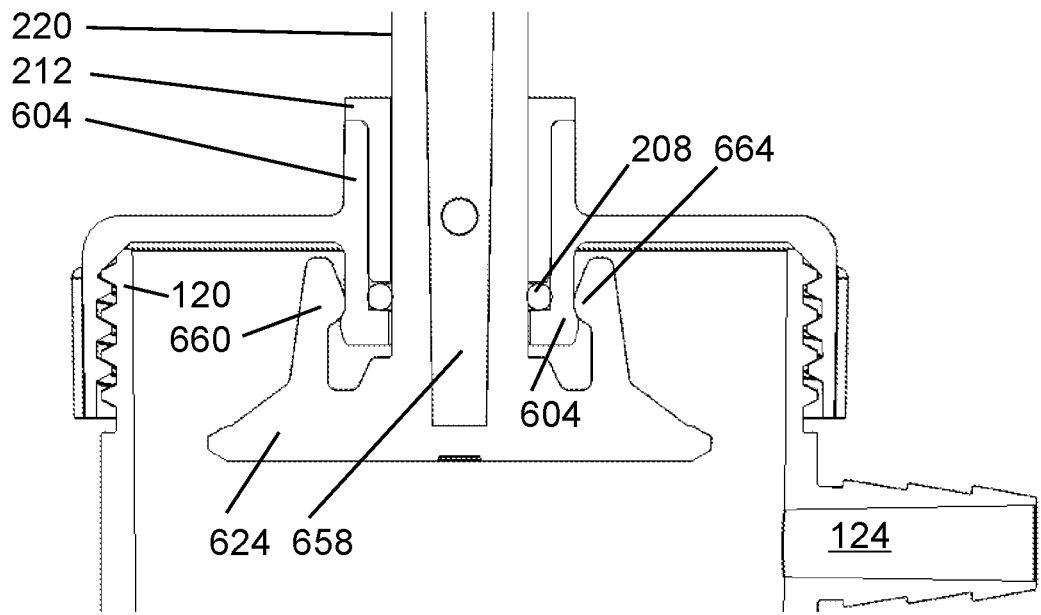
FIG. 20 is a cross section of a portion of a surgical collection assembly 600 of FIG. 15 with the cross section taken through the longitude of the inlet 124 of the jar 120.

FIG. 20 is a cross section of a portion of a surgical collection assembly 600 of FIG. 15 with the cross section taken through the longitude of the inlet 124 of the jar 120. To avoid clutter, basket 454 and finger ring 500 have been hidden.

FIG. 20 includes previously discussed items, jar 120, inlet 124, O-ring 208, bushing 212, and plunger rod 220. A plate brace 658 is extending outward from the page and is identified.

The two cap hooks 660 are shown reversibly engaged with portions of the cap 604.

Figure 21:
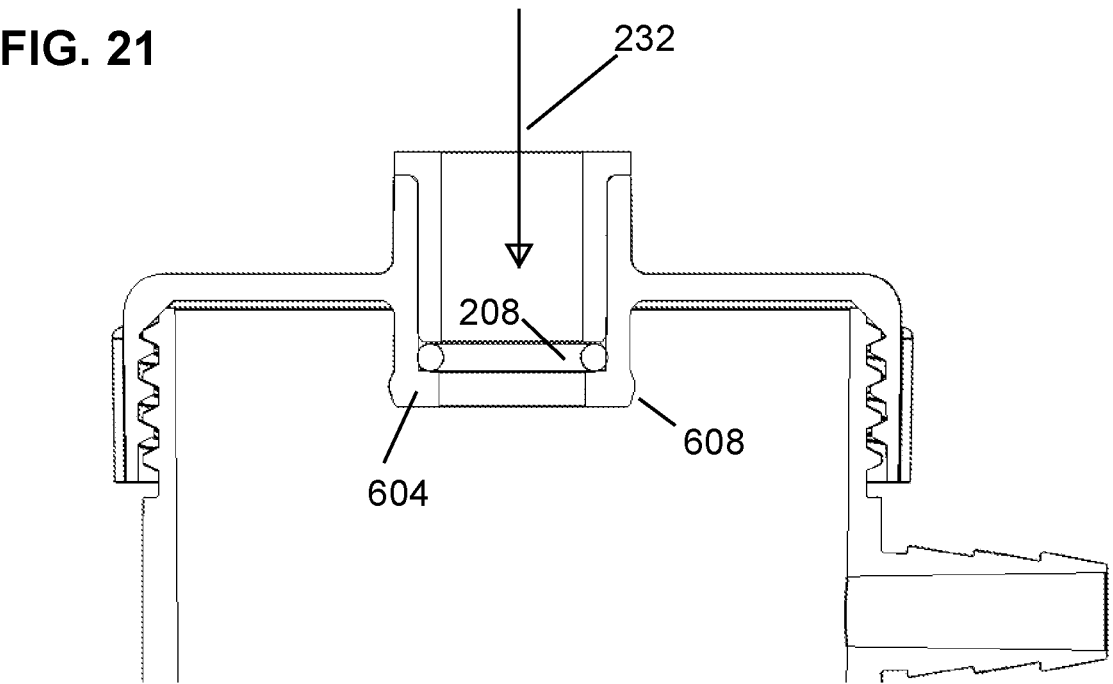
FIG. 21 is the same cross section of a portion of a surgical collection assembly 600 of FIG. 15 as shown in FIG. 20 but with the plunger device 650 now hidden.

FIG. 21 is the same cross section of a portion of a surgical collection assembly 600 of FIG. 15 as shown in FIG. 20 but with the plunger device 650 now hidden. In this view, an engagement ring 608 on the distal plunger plate side of the cap 604 is visible. This engagement ring 608 causes the cap hooks 660 to elastically deform while moving towards the plunger rod handle 240 until the protrusions 664 of the cap hooks 660 are on the handle-side of the engagement ring 608. This engagement is reversible as movement of the plunger rod handle 240 in a distal direction overcomes the engagement as the cap hooks 660 elastically deform to move the protrusions 664 distal relative to the engagement ring 608.

While the cap and plunger shapes discussed above are an efficient way to implement teachings of the present disclosure, this is not the sole manner of using these teachings. One of skill in the art could design the cap to have structures analogous to the cap hooks which elastically deform to reversibly engage an engagement ring that is part of the plunger device. One of skill in the art could choose to have elastic deformation happen during the engagement process for components on both the cap and the plunger device.

One could implement an interaction between the plunger device and features on the proximal end of the jar which would support a reversible engagement of the plunger device and the proximal end of the jar so that the reversible engagement retains the distal end plate in a fixed relationship relative to the jar cap until the user applies force to end the reversible engagement. One of skill in the art will appreciate that this may require the plunger device to be disengaged from the jar when the jar cap is being rotated relative to the jar 120 to engage or disengage the threaded proximal end of the jar 120.

Process of Use.

Figure 22:
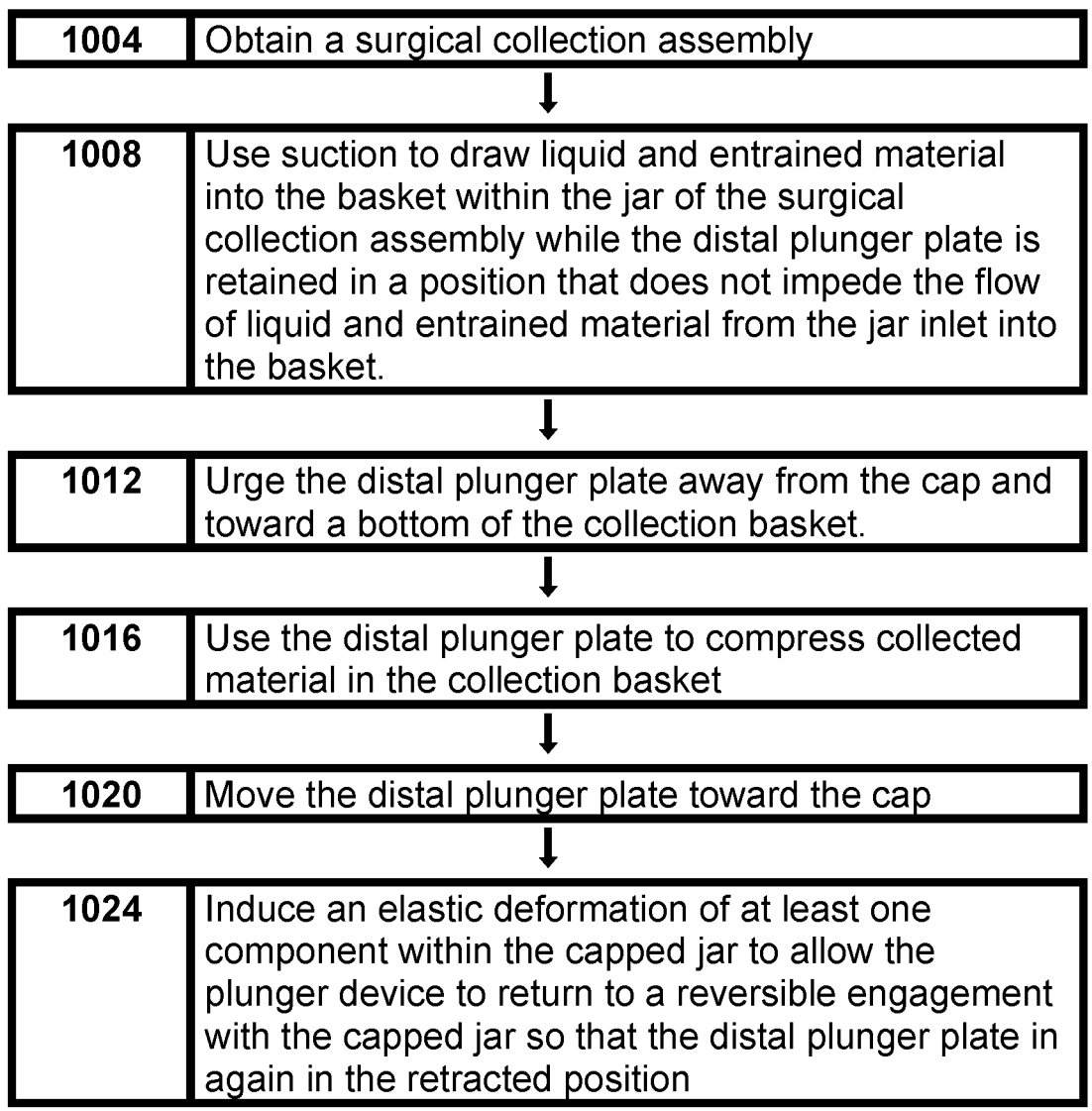
FIG. 22 shows the process 1000 for disengaging a plunger device from a surgical collection assembly and re-engaging the plunger device with the surgical collection assembly.

FIG. 22 shows the process 1000 for disengaging a distal plunger plate from a surgical collection assembly and re-engaging the plunger device with the surgical collection assembly. Details of the steps are set forth below.

1004—Obtain a surgical collection assembly with a jar containing a collection basket for filtering material obtained from liquid obtained during surgery. The jar having an inlet near the open end of the jar and an outlet near the bottom of the jar. The jar having a cap that is reversibly engaged with the jar to form a capped jar. The cap having a plunger device with a plunger rod and a distal plunger plate for use in compressing material collected in the filter basket. The distal plunger plate in a retracted position so that the distal plunger plate does not interfere with the ingress of liquid and entrained material obtained during surgery which flows through a jar inlet and into the collection basket.

1008—Use suction to draw liquid and entrained material into the basket within the jar of the surgical collection assembly while the distal plunger plate is retained in a position that does not impede the flow of liquid and entrained material from the jar inlet into the basket.

1012—Interacting with a portion of the plunger assembly that is external to the cap and jar to urge the distal plunger plate away from the cap and toward the bottom of the collection basket. The user inducing an elastic deformation of at least one component within the capped jar to release the plunger device from a reversible engagement with the capped jar.

1016—Using the distal plunger plate to compress collected material in the collection basket.

1020—Moving the distal plunger plate in a proximal direction which is away from the bottom of the collection basket and toward the cap.

1024—Inducing an elastic deformation of at least one component within the capped jar to allow the plunger device to return to a reversible engagement with the capped jar so that the distal plunger plate is again in the retracted position so that the distal plunger plate does not interfere with the ingress of liquid and entrained material obtained during surgery which flows through a jar inlet and into the collection basket in the event that additional liquid and entrained material is obtained.

As noted above, the elastic deformation may happen to a portion of:
the plunger device such as cap hooks 660;
the cap such as finger springs 710 or inward protrusions 754; or
the jar.

The interacting with a portion of the plunger assembly may happen through interaction with a plunger rod handle at a proximal end of the plunger device or through interaction with a plunger rod.

The distal plunger plate may be placed in the retracted position after use of the distal plunger plate to compress the collected material. This placement in the retracted position may come after removing the first collection basket and inserting a different collection basket for use in collecting additional material.

ALTERNATIVES AND VARIATIONS

Engagement With A Bushing Disc.

Figure 23:
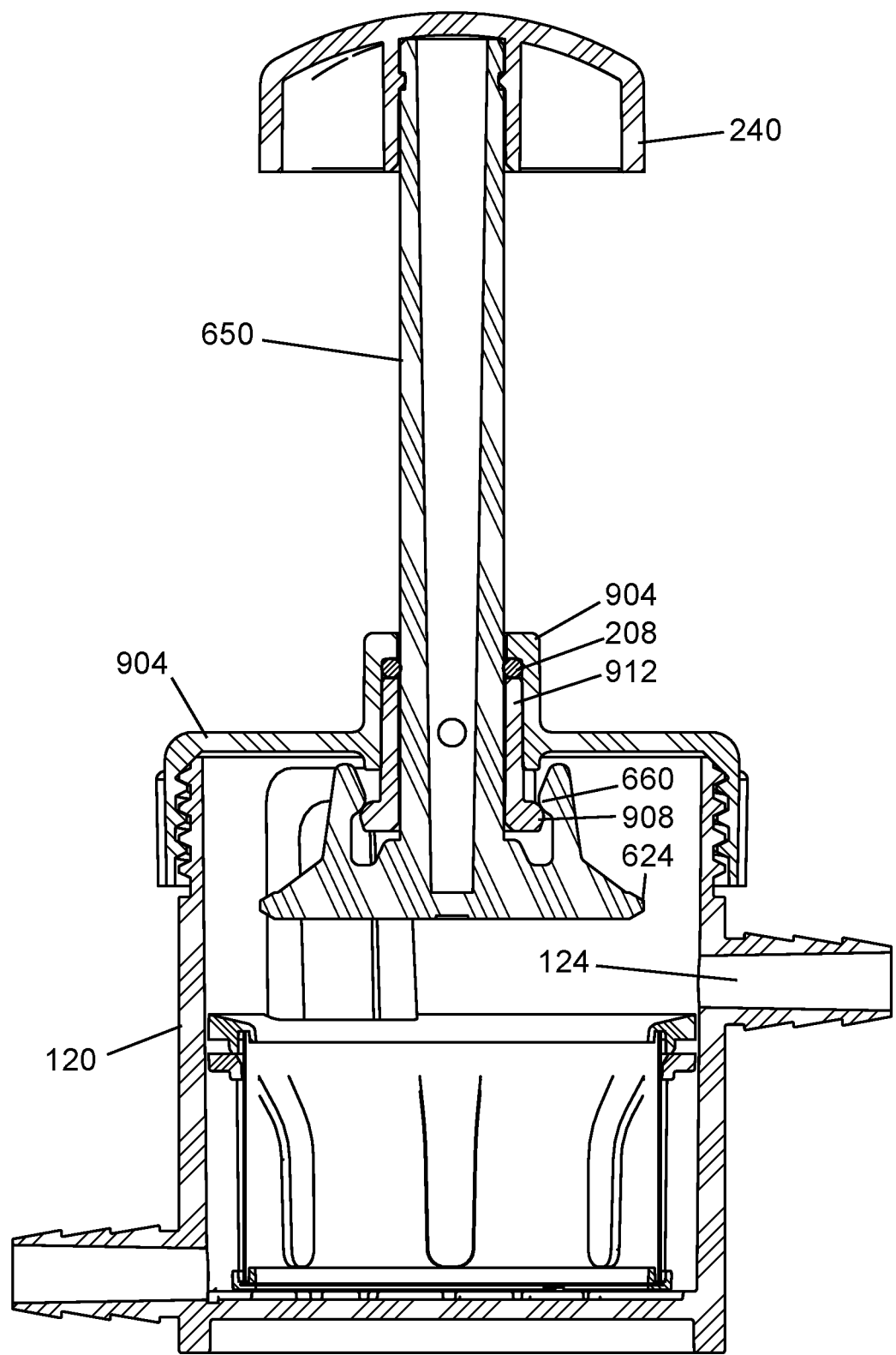
FIG. 23 shows a cross section of a plunger assembly 920.

FIG. 21 illustrates an engagement ring 608 that is an integral part of the cap 604. A variation of this idea is shown in FIG. 23. FIG. 23 shows a cross section of a plunger assembly 920. The plunger device 650 may be identical to that discussed in connection with plunger assembly 620 discussed above. However, instead of a cap 604 that receives an O-ring 208 and bushing 212 from the top side, plunger assembly 920 has a cap 904 that receives an O-ring 208 and bushing 912 from the side of the cap 904 that faces the jar 120. The bushing 912 is inserted up into the cap 904 to trap the O-ring 208 as part of the assembly process for plunger assembly 920. Once assembled, the cap hooks 660 on the distal plunger plate 624 of the plunger device 650 can elastically deform to become reversibly engaged with an engagement ring 908 on bushing 912. Once engaged, the distal plunger plate 624 is retained above the inlet 124 and does not impede the movement of material into the jar 120. When the plunger plate 624 is needed to press the collected material, downward pressure on the plunger rod handle 240 will overcome the spring force of the cap hooks 660 and release the distal plunger plate 624 from the engagement ring 908 on bushing 912.

After use of the distal plunger plate 624, the distal plunger plate 624 can be reengaged with the engagement ring 908 on bushing 912 by pulling up on the plunger rod handle 240 until the cap hooks 660 engage again with the engagement ring 908 on bushing 912.

Figure 24:
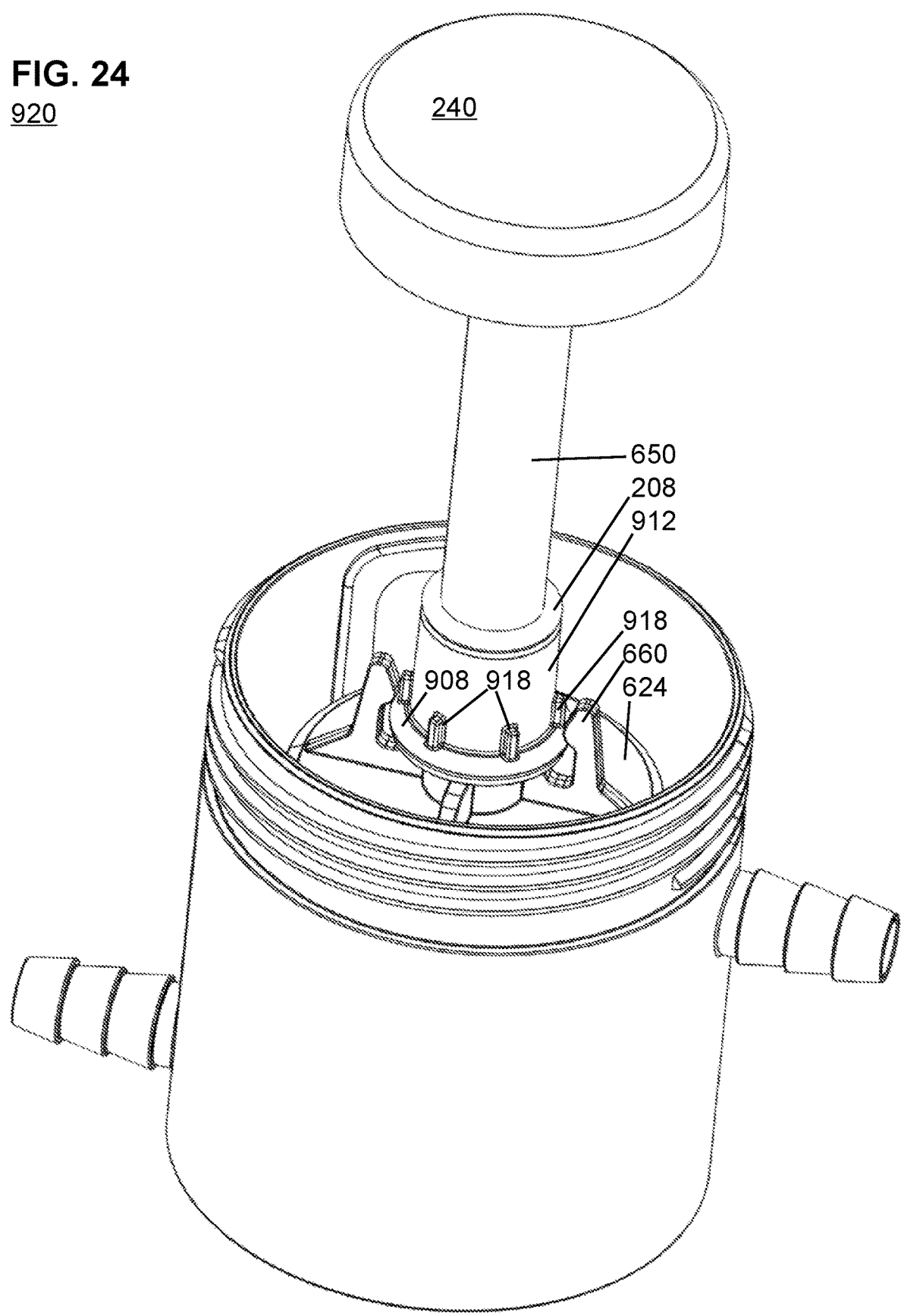
FIG. 24 is a top perspective view of plunger assembly 920 that has been modified to make the cap 904 invisible in order to allow a clear view of the interaction of bushing 912 and distal plunger plate 624.

FIG. 24 shows the plunger assembly 920 of FIG. 23. FIG. 24 is a top perspective view that has been modified to make the cap 904 invisible in order to allow a clear view of the interaction of bushing 912 and distal plunger plate 624. The engagement ring 908 of the bushing 912 may be stabilized by a series of connection buttresses 918. As the connection buttresses 918 do not extend far enough to interfere with the cap hooks 660, there is not a need to align the cap hooks 660 with respect to the connection buttresses 918.

Elastically Deformed Items not on Plunger Device.

Figure 25:
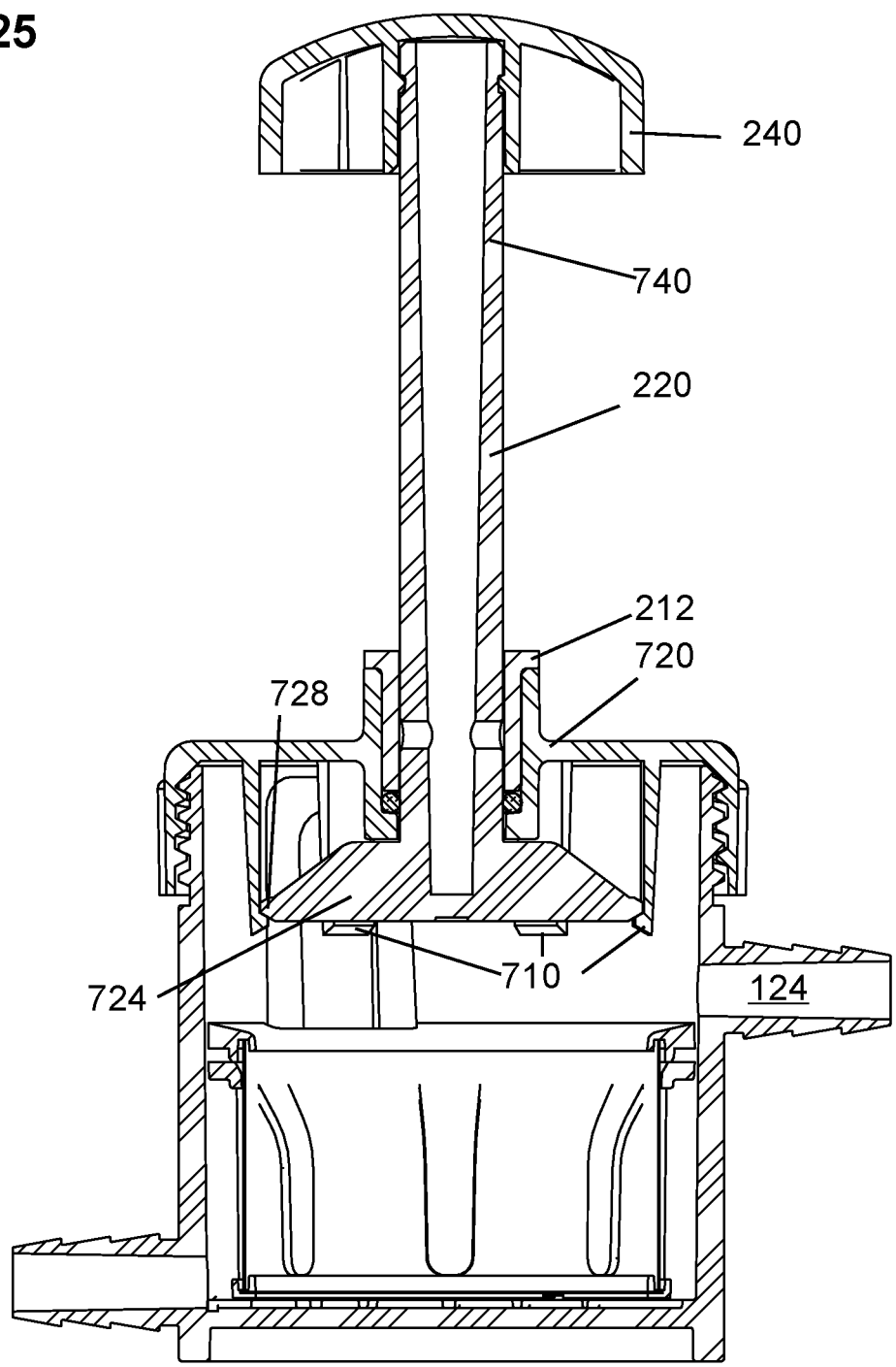
FIG. 25 shows a cross section of surgical collection assembly 700 with plunger device 740.

FIG. 25 shows a cross section of surgical collection assembly 700 with plunger device 740. Cap 720 has a set of distally protruding finger springs 710 that can reversibly engage a beveled perimeter 728 of distal plunger plate 724. A user moving the distal plunger plate 724 in a proximal direction will cause the beveled perimeter 728 to temporarily elastically deform the set of finger springs 710 which then retain the distal plunger plate 724 in a position closer to the plunger rod handle 240 than the inlet 124 is to the plunger rod handle 240. In this reversible engagement, the distal plunger plate 724 does not interfere with the ingress of liquid and entrained material obtained during surgery which flows through the inlet 124 into the basket within the jar 120.

The engagement of the finger springs 710 with the distal plunger plate 724 is ended when a user moves the plunger rod handle 240 in a distal direction. Free of the engagement with the finger springs 710, the distal plunger plate 724 may be moved to the bottom of the basket to compress the collected material.

Figure 26:
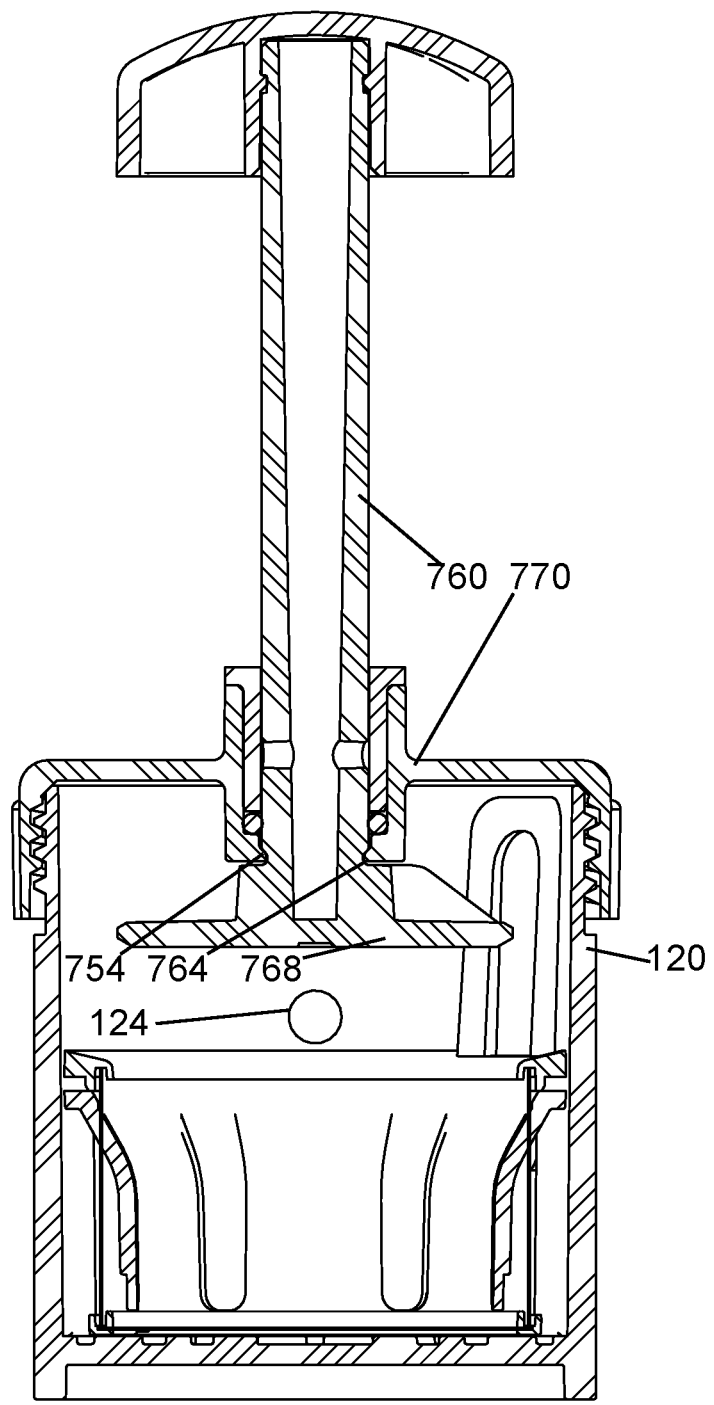
FIG. 26 shows a cross section of surgical collection assembly 750 with plunger device 760.

FIG. 26 shows a cross section of surgical collection assembly 750 with plunger device 760. Cap 770 has a set of inward protrusions 754 that can reversibly engage a retention ring 764 on plunger device 760 near distal plunger plate 768.

A user moving the distal plunger plate 768 in a proximal direction will cause the set of inward protrusions 754 to flex outward and then reversibly engage the retention ring 764 on plunger device 760 near distal plunger plate 768. In this reversible engagement, the distal plunger plate 768 does not interfere with the ingress of liquid with entrained material obtained during surgery which flows through the inlet 124 into the basket within the jar 120.

A user subsequently moving the distal plunger plate 768 in a distal direction will cause the set of inward protrusions 754 to flex outward and then reversibly disengage the retention ring 764 on plunger device 760 near distal plunger plate 768. Free of the engagement, the distal plunger plate 768 may be moved to the bottom of the basket to compress the collected material.

Transitory and Non-Transitory Elastic Deformation.

Those of skill in the art will appreciate that elastic deformation of at least one component during the state change of the distal plunger plate from retained to not retained or from not retained to retained may be a transitory elastic deformation so that none of the components in the plunger assembly are in a sustained elastic deformation attributable to the retention of the distal plunger plate.

Conversely, at least one component may be maintained in elastic deformation for as long as the distal plunger plate is being retained.

In FIG. 20, cap hooks 660 will remain in elastic deformation for as long as distal plunger plate 624 is in a retained position. In FIG. 25, the finger springs 710 could be designed such that the finger springs 710 remained in elastic deformation for as long as the distal plunger plate 624 is in a retained position or they could be designed to be in a state without elastic deformation while the distal plunger plate 624 is in a retained position. In FIG. 26, the cap 770 will remain in plastic deformation while the distal plunger plate 768 is held in the retained position. But this could be changed so that the cap 770 would not remain in plastic deformation while the distal plunger plate 768 was held in the retained position if the depth of the retention ring 764 in the plunger device 760 was sufficient to receive the inward protrusions 754 of the cap 770.

Drape Clip.

Surgical collection assemblies of the type discussed in this disclosure are used as part of a surgical procedure. While the surgical collection assemblies provide an essential function in collecting bone dust or other target material, during the surgery that is creating the liquid with entrained material to be filtered, the surgical collection assembly is not the center of attention. It is thus advantageous to be able to position the surgical collection assembly in a manner where you can set it and forget it. As bone dust is precious for use in subsequent activities within certain surgical procedures, it is desirable to reduce the chance that the surgical collection assembly will fall off the operating table and leave the sterile field. Thus, a drape clamp 800 to affix the tubing associated with the surgical collection assembly to a surgical drape or other item within the sterile field would be helpful.

Figure 27:
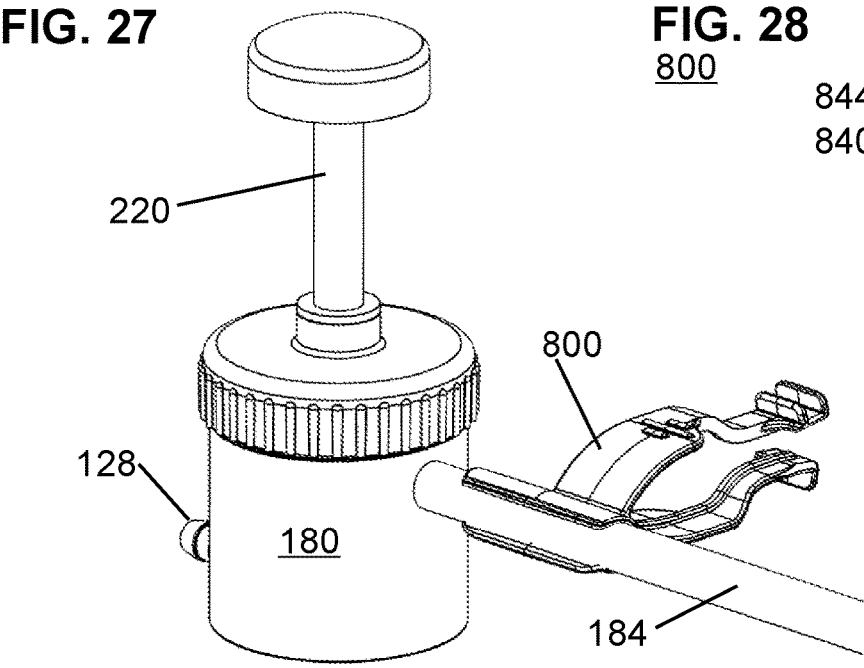
FIG. 27 shows a perspective view of a surgical collection assembly 180.

FIG. 27 shows a perspective view of a surgical collection assembly 180. For purposes of the discussion of drape clamp 800 the specifics of how the distal plunger plate is retained out of the way of the material coming into the surgical collection assembly 180 are not relevant. A drape clamp 800 may even be used with a surgical collection assembly that uses a spring 260 (FIG. 1). Tubing 184 carries material to the inlet 124 (FIG. 1) of the surgical collection assembly 180.

Figure 28:
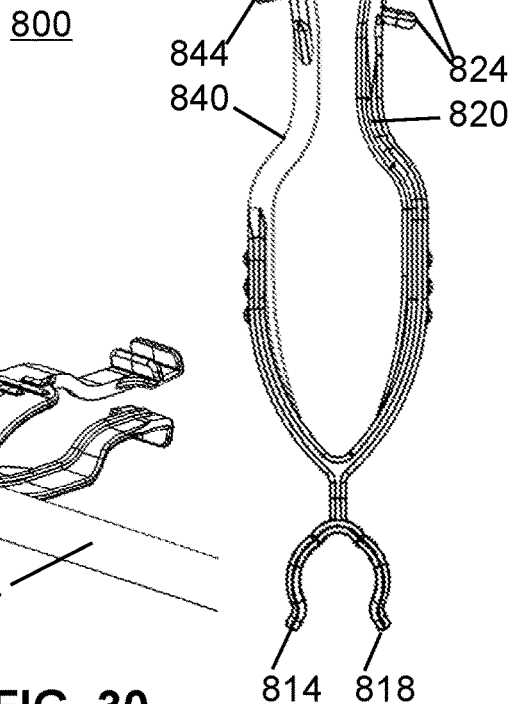
FIG. 28 is a top view of a drape clamp 800 in the open position.

FIG. 28 is a top view of a drape clamp 800 in the open position. The drape clamp 800 has a first tubing leg 814 and a second tubing leg 818 that elastically deform to allow the insertion of the inlet tubing 184 and then attempt to return to their original shapes. This attempt to return to the original undeformed shapes of the tubing legs 814 and 818 results in an interference fit around inlet tubing 184. One of skill in the art will appreciate that alternatively, the drape clamp 800 could be engaged with tubing on the suction side that is connected with outlet 128.

Upper leg 820 has a set of one or more locking fingers 824. Lower leg 840 has a set of one or more locking fingers 844. The drape clamp 800 is used by crossing the upper leg 820 and the lower leg 840. The elastic deformation of the legs 820 and 840 to make them cross results in both legs being under spring force to move back to their original positions. This causes the set of one or more locking fingers 824 to press against lower leg 840 and the set of one or more locking fingers 844 to press against lower leg 820 (assuming that the fingers are sized so both sets of fingers make contact with the other leg). By positioning these sets of locking fingers on opposite sides of a drape before releasing the upper leg 820 and the lower leg 840, the drape is forced into a serpentine shape to partially conform to the peaks and valleys created by the interleaved locking fingers 824 and 844.

Figure 29:
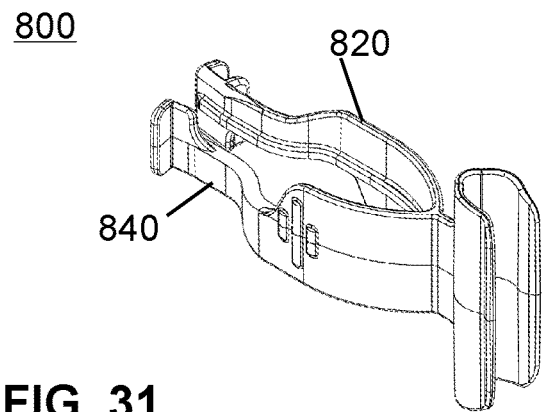
FIG. 29 is a perspective view of the drape clamp 800 in an open position with the upper leg 840 and the lower leg 820 in a resting position without any elastic deformation or resulting spring forces.

FIG. 29 is a perspective view of the drape clamp 800 in an open position with the upper leg 840 and the lower leg 820 in a resting position without any elastic deformation or resulting spring forces.

Figure 30:
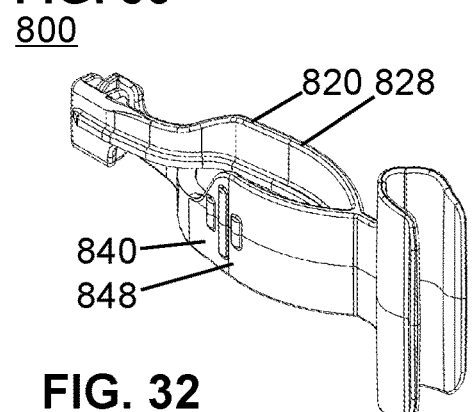
FIG. 30 is a perspective view of the drape clamp 800 in a closed position with the upper leg 840 and the lower leg 820 in elastic deformation with resulting spring forces that drive the locking fingers 824 and 844 (FIG. 27) in a manner that would retain an engaged portion of drape material or another anchor point in the sterile field.

FIG. 30 is a perspective view of the drape clamp 800 in a closed position with the upper leg 840 and the lower leg 820 in elastic deformation with resulting spring forces that drive the locking fingers 824 and 844 (FIG. 27) in a manner that will retain an engaged portion of drape material or another anchor point in the sterile field. One of skill in the art will recognize that pressing leg portion 828 and leg portion 848 towards one another would create an opening between the sets of locking fingers 824 and 844. This position of the drape clamp 800 with the legs crossed but the fingers separated may be called hyper-crossed.

Figure 31:
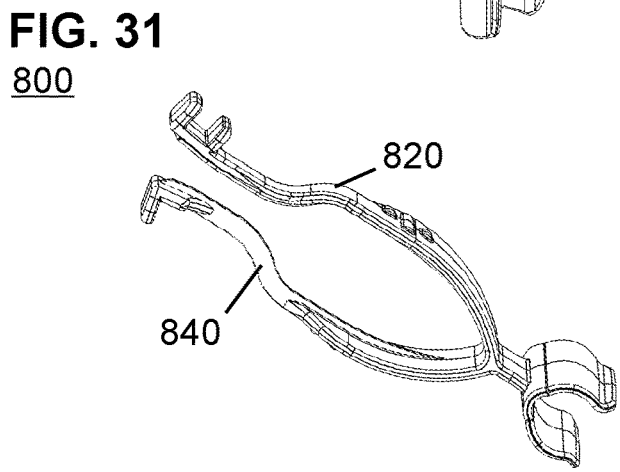
FIG. 31 is a perspective view of the drape clamp 800 in an open position with the upper leg 840 and the lower leg 820 in a resting position without any elastic deformation or resulting spring forces.

FIG. 31 is a perspective view of the drape clamp 800 in an open position with the upper leg 840 and the lower leg 820 in a resting position without any elastic deformation or resulting spring forces. FIG. 31 is rolled slightly from the view in FIG. 29 to provide another vantage point.

Figure 32:
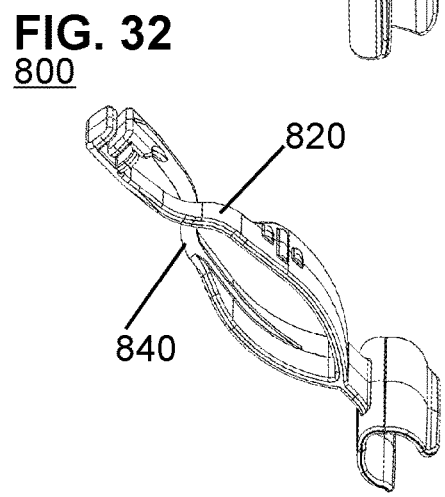
FIG. 32 is a perspective view of the drape clamp 800 in a closed position with the upper leg 840 and the lower leg 820 in elastic deformation with resulting spring forces that drive the locking fingers 824 and 844 (FIG. 27) in a manner that would retain an engaged portion of drape material or another anchor point in the sterile field.

FIG. 32 is a perspective view of the drape clamp 800 in a closed position with the upper leg 840 and the lower leg 820 in elastic deformation with resulting spring forces that drive the locking fingers 824 and 844 (FIG. 27) in a manner that would retain an engaged portion of drape material or another anchor point in the sterile field. FIG. 32 is rolled slightly from the view in FIG. 30 to provide another vantage point.

Use of a Drape Clip to Hold Distal Plunger Plate Up.

Figure 33:
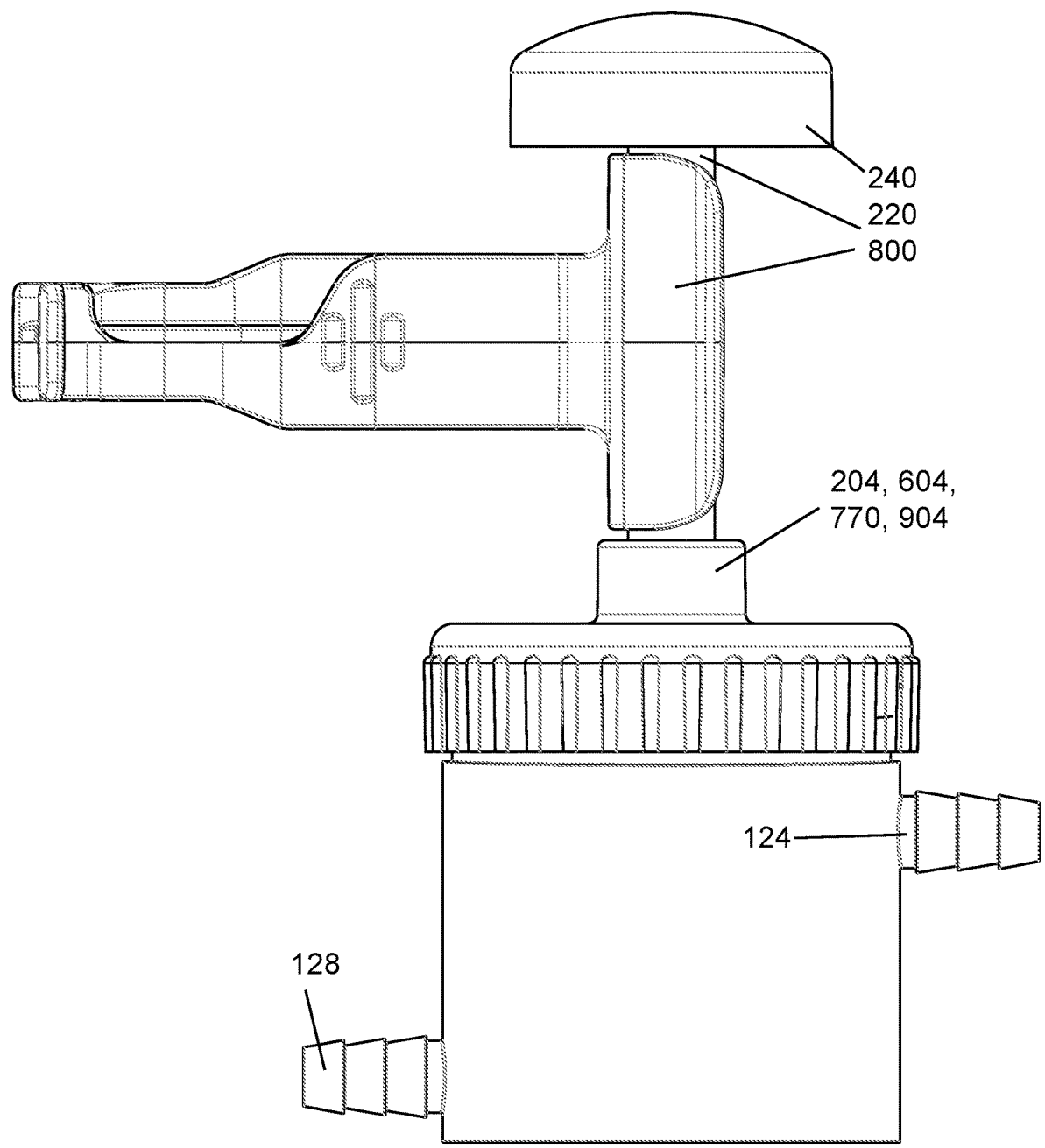
FIG. 33 shows a drape clip 800 engaged with a plunger rod 220 to hold the plunger rod handle 240 in an elevated position away from the jar cap (such as 204, 604, 770, and 904) and thus hold the distal plunger plate (not visible here) up above the inlet 124.

FIG. 33 shows a drape clip 800 engaged with a plunger rod 220 to hold the plunger rod handle 240 in an elevated position away from the jar cap (such as 204, 604, 770, and 904) and thus hold the distal plunger plate (not visible here) up above the inlet 124. The use of a drape clip 800 to hold the distal plunger plate up may be done in two circumstances.

The drape clip 800 may serve as the sole mechanism to hold the distal plunger plate in the elevated position. In other words the surgical collection assembly may not have any other mechanism (such as a spring around plunger rod 220) or an engagement between the plunger assembly and the jar cap assembly that would otherwise hold the distal plunger plate in the elevated position. The drape clip 800 may engage the drape during the collection of fluids and entrained materials if that is deemed useful by the team doing the procedure. If the drape clip 800 is engaged with the drape, the drape clip 800 would do so while still engaged with the plunger rod 220. When the team wishes to compress the collected material, the drape clip 800 would be disengaged from the plunger rod 220 so that the distal plunger plate can compress the collected material. Afterwards, the drape clip 800 can be re-engaged with the plunger rod 220 to hold the distal plunger plate in the elevated position for additional collection of material.

Alternatively, the drape clip 800 may serve as a supplemental mechanism to hold the distal plunger plate in the elevated position. For example, the drape clip 800 may be applied to the plunger rod 220 before shipping the assembled surgical collection assembly. This supplemental retention would avoid an unintended release of an engagement between the plunger assembly and the jar cap assembly from an event such as a drop of the shipping box. Thus, a distal plunger plate would be prevented from being down below the jar inlet 124 from the jolt during shipping.

Note, the use of a drape clip 800 to retain the distal plunger plate is independent of the internal geometries of the plunger assembly and the jap cap assembly and may be used with a plunger assembly/jar cap assembly that differs from any described in this application as long as there is a plunger rod 220 which may be used to elevate the distal plunger plate.

One of skill in the art will appreciate that the number of fingers could be one or more. The number of fingers on each leg could be N and N+1 or each leg could have the same number fingers but offset. For example, upper leg 820 may have a set of two locking fingers 824 and lower leg 840 may also have a set of two locking fingers 844 which are offset so that the combination of the locking fingers forms a serpentine path for a captured portion of a surgical drape.

One of skill in the art will appreciate that making the entire drape clamp 800 from one material will simplify the manufacturing process. However, using just one material is a design choice but not a requirement of this disclosure. One could make a drape clamp 800 with one leg that is much stiffer than the material used for the other leg. In such a drape clamp, the elastic deformation from crossing one leg over the other leg would fall almost entirely on the more flexible leg. Thus, it is possible that the stiff leg would not undergo substantial elastic deformation and not have a substantial spring force to return to an undeformed shape. However, whether coming from one leg or two, there would still be a spring force that causes the drape clamp to engage with a trapped portion of a surgical drape as at least one leg would be forcing the fingers towards the other leg.

A suitable material for use in making a drape clamp 800 would be a polymer such as polypropylene. Other materials including metals could be selected to provide appropriate spring forces.

Process of Use.

FIG. 34 shows the process 2000 for connecting a surgical collection assembly and associated tubing to a drape within a sterile field. Details on the steps are set forth below.

2004—Connect a drape clamp to the combination of the surgical collection assembly and associated tubing. The connection could be to tubing engaged with the surgical collection assembly on either the inlet 124 or to the outlet 128. While the drape clamp 800 may be placed close to the surgical collection assembly on tubing directly above the inlet 124 or to the outlet 128, the drape clamp may be a bit further out so that drape clamp 800 is not directly over inlet 124 or outlet 128. Alternatively, the drape clamp could be engaged with the plunger rod 220 (FIG. 33) or another portion of the surgical collection assembly. The drape clamp could be connected to the surgical collection assembly before delivery to the operating room. The drape clam could be connected while the surgical collection assembly after delivery to the operating room.

2008—Hyper-cross the legs of the drape clamp so that there is elastic deformation within the drape clamp and thus a spring force to move the one or both legs back to their original positions and there is a gap between the one or more fingers on one leg and the one or more fingers on the other leg.

2012—Insert a portion of drape material in a gap between fingers of the drape clamp while the drape clamp legs are hyper-crossed.

2016—Release the drape clamp so that the fingers on each crossed leg move toward the other leg to form a serpentine path for the captured drape material to form a reversible engagement between the surgical collection assembly and the drape.

Those of skill in the art will appreciate that process 2000 will work if the portion of drape material is an edge of the drape or that process 2000 will work if the surgical drape is folded over and thus two layers of drape are captured by the drape clamp.

Those of skill in the art will appreciate that the connection of the drape clamp to the drape may precede the connection of the drape clamp to the combination of the surgical collection assembly and associated tubing.

It is less likely but possible that a user might connect the drape clamp to tubing before the tubing is connected to the inlet or outlet of the surgical collection assembly. The scope of this disclosure embraces this variation as well as the more likely sequence of attaching the tubing first.

Use of a Split Sleeve to Hold Distal Plunger Plate Up.

Figure 35:
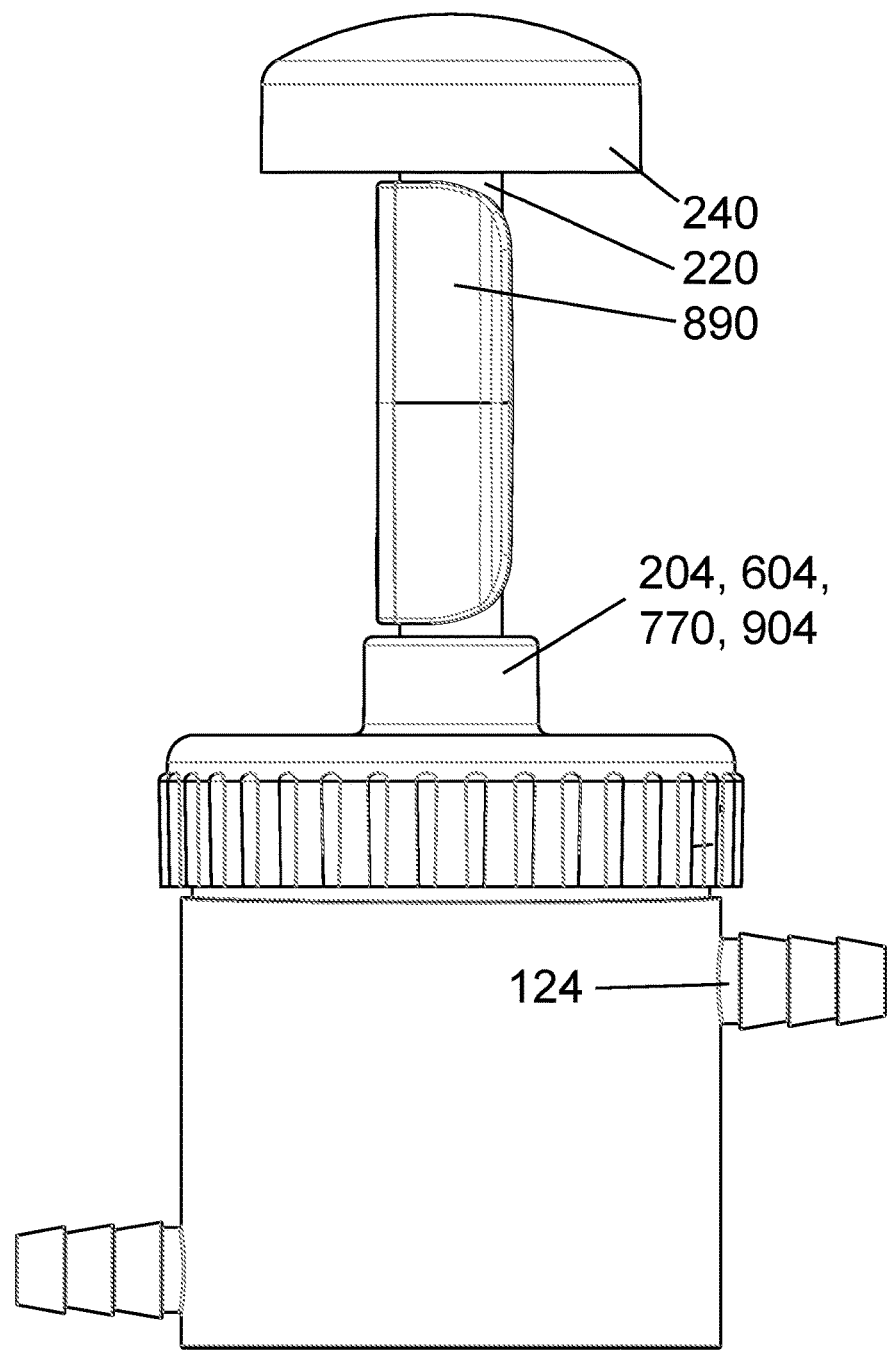
FIG. 35 shows a split sleeve 890 engaged with a plunger rod 220 to hold the plunger rod handle 240 in an elevated position away from the jar cap (such as 204, 604, 770, and 904) and thus hold the distal plunger plate (not visible here) up above the inlet 124.

FIG. 35 shows a split sleeve 890 engaged with a plunger rod 220 to hold the plunger rod handle 240 in an elevated position away from the jar cap (such as 204, 604, 770, and 904) and thus hold the distal plunger plate (not visible here) up above the inlet 124. The use of a split sleeve 890 to hold the distal plunger plate up may be done in two circumstances.

The split sleeve 890 may serve as the sole mechanism to hold the distal plunger plate in the elevated position. In other words the surgical collection assembly may not have any other mechanism (such as a spring around plunger rod 220) or an engagement between the plunger assembly and the jar cap assembly that would otherwise hold the distal plunger plate in the elevated position. The split sleeve 890 may engage the drape during the collection of fluids and entrained materials if that is deemed useful by the team doing the procedure. If the split sleeve 890 is engaged with the drape, the split sleeve 890 would do so while still engaged with the plunger rod 220. When the team wishes to compress the collected material, the split sleeve 890 would be disengaged from the plunger rod 220 so that the distal plunger plate can compress the collected material. Afterwards, the split sleeve 890 can be re-engaged with the plunger rod 220 to hold the distal plunger plate in the elevated position for additional collection of material.

Alternatively, the split sleeve 890 may serve as a supplemental mechanism to hold the distal plunger plate in the elevated position. For example, the split sleeve 890 may be applied to the plunger rod 220 before shipping the assembled surgical collection assembly. This supplemental retention would avoid an unintended release of an engagement between the plunger assembly and the jar cap assembly from an event such as a drop of the shipping box. Thus, a distal plunger plate would be prevented from being down below the jar inlet 124 from the jolt during shipping.

Note, the use of a split sleeve 890 to retain the distal plunger plate is independent of the internal geometries of the plunger assembly and the jap cap assembly and may be used with a plunger assembly/jar cap assembly that differs from any described in this application as long as there is a plunger rod 220 which may be used to elevate the distal plunger plate.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

Where methods and/or events described above indicate certain events and/or procedures occurring in a certain order, the ordering of certain events and/or procedures may be modified. Additionally, certain events and/or procedures may be performed concurrently in a parallel process when possible, as well as performed sequentially as described above.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. A process for disengaging a plunger device from a jar cap assembly and subsequently re-engaging the plunger device with the jar cap assembly, the process comprising:
    obtaining a surgical collection assembly comprising:
    a collection jar with a collection basket;
    a jar cap assembly; and
    the plunger device with a distal plunger plate;
    inducing a temporary elastic deformation in order to disengage the plunger device from a reversible retention in a retracted position so that the distal plunger plate does not interfere with a flow path for ingress of liquid through an inlet port to the collection jar;
    moving the distal plunger plate away from the jar cap assembly;
    using the distal plunger plate to compress collected material in the collection basket;
    moving the distal plunger plate in a proximal direction which is away from a bottom of the collection basket and toward the jar cap assembly; and
    engaging plunger device with the jar cap assembly in the reversible retention with the distal plunger plate in the retracted position that does not interfere with a flow path for an ingress of liquid through the inlet port to the collection jar by elastically deforming at least one component in the surgical collection assembly.

2. The process of claim 1 wherein engaging the plunger device with the jar cap assembly includes an elastic deformation of at least one component attached to the distal plunger plate.

3. The process of claim 1 wherein engaging the plunger device with the jar cap assembly includes an elastic deformation of at least one component attached to the jar cap assembly.

4. The process of claim 1 wherein engaging the plunger device with the jar cap assembly includes an elastic deformation of the collection jar.

5. The process of claim 1 wherein engaging the plunger device with the jar cap assembly includes an elastic deformation substantially aligned with a radial line from a longitudinal axis of the plunger device.

6. The process of claim 1 wherein engaging the plunger device with the jar cap assembly includes an elastic deformation not substantially aligned with any radial line originating from a longitudinal axis of the plunger device.

7. The process of claim 1 wherein engaging the plunger device with the jar cap assembly includes an elastic deformation that is transitory and ceases once the plunger device is in the reversible retention in the retracted position.

8. The process of claim 1 wherein engaging the plunger device with the jar cap assembly includes an elastic deformation that continues while the plunger device is in the reversible retention in the retracted position.

9. The process of claim 1 wherein engaging the plunger device with the jar cap assembly includes engaging the distal plunger plate with the jar cap assembly.

10. The process of claim 1 wherein engaging the plunger device with the jar cap assembly includes engaging components attached to the distal plunger plate with the jar cap assembly.

11. The process of claim 1 wherein engaging the plunger device with the jar cap assembly includes engaging at least one retention feature on a portion of a plunger rod that moves through a bore in the jar cap assembly with a portion of the jar cap assembly.

* * * * *